United States Patent
Mizukami et al.

(10) Patent No.: US 9,517,210 B2
(45) Date of Patent: Dec. 13, 2016

(54) METHOD FOR PRODUCING MICROCAPSULE POWDER

(71) Applicant: TAKEDA PHARMACEUTICAL COMPANY LIMITED, Osaka-shi, Osaka (JP)

(72) Inventors: Seitaro Mizukami, Osaka (JP); Naoki Choda, Osaka (JP)

(73) Assignee: TAKEDA PHARMACEUTICAL COMPANY LIMITED, Osaka-Shi (JP)

( * ) Notice: Subject to any disclaimer, the term of this patent is extended or adjusted under 35 U.S.C. 154(b) by 41 days.

(21) Appl. No.: 14/405,010

(22) PCT Filed: Jul. 10, 2013

(86) PCT No.: PCT/JP2013/068809
§ 371 (c)(1),
(2) Date: Dec. 2, 2014

(87) PCT Pub. No.: WO2014/010614
PCT Pub. Date: Jan. 16, 2014

(65) Prior Publication Data
US 2015/0132394 A1 May 14, 2015

(30) Foreign Application Priority Data
Jul. 12, 2012 (JP) .................. 2012-156390

(51) Int. Cl.
*A61K 9/52* (2006.01)
*A61K 9/50* (2006.01)
(Continued)

(52) U.S. Cl.
CPC ........... *A61K 9/5089* (2013.01); *A61K 9/5026* (2013.01); *A61K 9/5031* (2013.01); *A61K 38/24* (2013.01);
(Continued)

(58) Field of Classification Search
CPC ............... B04C 1/00; B04C 5/00; B04C 5/04; A61K 9/50; A61K 9/5005; A61K 9/5031
See application file for complete search history.

(56) References Cited

U.S. PATENT DOCUMENTS 2,992,141 A * 7/1961 Peebles .................. A23C 21/00
127/31
4,011,661 A * 3/1977 Sezaki ................. A61K 9/0019
34/389

(Continued)

FOREIGN PATENT DOCUMENTS

EP    1 765 295 B1    9/2012
JP    61-271045    12/1986
(Continued)

OTHER PUBLICATIONS

International Search Report, Date of mailing: Sep. 10, 2013 (Sep. 10, 2013).
(Continued)

*Primary Examiner* — Lakshmi Channavajjala
(74) *Attorney, Agent, or Firm* — Rankin, Hill & Clark LLP

(57) ABSTRACT

A method for producing a microcapsule powder includes a concentration step. In the concentration step, an aqueous dispersion of a microcapsule is supplied into a cyclone, and the aqueous dispersion is then concentrated. The concentration step includes an aqueous dispersion-supplying step and a concentrated dispersion-recovering step. In the aqueous dispersion-supplying step, the aqueous dispersion is supplied into a cylindrical member inlet. In the concentrated dispersion-recovering step, a microcapsule dispersion is recovered. The microcapsule dispersion is discharged through a conical member outlet.

6 Claims, 16 Drawing Sheets

(51) Int. Cl.
  *B04C 5/13*    (2006.01)
  *A61K 38/24*   (2006.01)
  A61K 38/00    (2006.01)
  A61J 3/07     (2006.01)

(52) U.S. Cl.
  CPC  *B04C 5/13* (2013.01); *A61J 3/077* (2013.01); *A61K 38/00* (2013.01); *F04C 2270/0421* (2013.01)

(56) References Cited

U.S. PATENT DOCUMENTS

2004/0118007 A1    6/2004  Chickering, III et al.
2007/0155906 A1*   7/2007  Hissink ............... A61K 9/1647
                                                      525/242

FOREIGN PATENT DOCUMENTS

| JP | 62-114300   | 7/1987 |
| JP | 6-63452     | 3/1994 |
| JP | 2008-505057 | 2/2008 |
| WO | 96/15814 A1 | 5/1996 |
| WO | 03/002091 A2| 1/2003 |

OTHER PUBLICATIONS

Gharsallaoui et al., "Applications of Spray-Drying in Microencapsulation of Food Ingredients: An Overview", Food Research International, Elsevier Applied Science, Barking, GB, vol. 40, No. 9, Sep. 18, 2007, 15 pages.
European Search Report dated Jul. 1, 2016, 9 pages.

* cited by examiner

METHOD FOR PRODUCING MICROCAPSULE POWDER

TECHNICAL FIELD

The present invention relates to a method for producing a microcapsule powder.

BACKGROUND ART

Patent Document 1 discloses a method for producing a microcapsule. In this method, a microcapsule is separated from an aqueous dispersion by a centrifuge and then subjected to a lyophilization step. More specifically, Patent Document 1 describes an example in which a disc centrifuge is used as the centrifuge.

PRIOR ART DOCUMENT

Patent Document

Patent Document 1: WO 03/002091

SUMMARY OF THE INVENTION

Problems to be Solved by the Invention

The method for producing a microcapsule disclosed in Patent Document 1, however, has a problem in productivity. This problem is explained below referring to in-water drying as an example. In-water drying comprises the following steps. A first step is a step of injecting a polymer and an organic solvent into water. A second step is a step of removing the organic solvent from the water. By this, a microcapsule solidifies in the water. The resultant is an aqueous dispersion of a microcapsule. A third step is a step of separating the microcapsule from the aqueous dispersion by a centrifuge. A fourth step is a step of lyophilizing the microcapsule.

The third step presents a cause of the low productivity. The third step requires a long time and therefore presents a cause of the low productivity. The same problem is presented by any method for producing a microcapsule where separation of a microcapsule from an aqueous dispersion is necessary.

The method for producing a microcapsule disclosed in Patent Document 1 requires much labor so as to ensure operator's safety. One of the reasons why much labor is required is in the third step. In the third step, an operator is exposed to a microcapsule. A microcapsule or a chemical substance adhering thereto can be harmful to the health of an operator. For protecting an operator from such a risk, much labor is required.

The present invention has for its object to solve such a problem. An object of the present invention is to enhance productivity in separating a microcapsule from an aqueous dispersion and reduce labor required for ensuring safety.

Solutions to the Problems

A method for producing a microcapsule powder of the present invention is explained below referring to drawings. Reference numerals from the drawings are used in this section so as to help understanding of the present invention. Use of the reference numerals from the drawings in this section does not intend to limit the scope of the present invention to the range shown in the drawings.

The inventors of the present invention conducted intensive research to solve the problem and, as a result, have found a method to use a cyclone for separating a microcapsule from an aqueous dispersion. Thus, the present invention has now been completed.

That is, the present invention is as follows.

[1] A method for producing a microcapsule powder, comprising a concentration step of supplying an aqueous dispersion of a microcapsule into a cyclone and then concentrating the aqueous dispersion.

[2] The method according to [1],
wherein
the cyclone comprises:
a cylindrical member having a cylindrical member inlet and defining a cylindrical space,
a conical member attached to one end of the cylindrical member, defining a conical space, and having a conical member outlet,
a tubular member attached to the other end of the cylindrical member and having a tubular member outlet,
the conical space communicating with the cylindrical space, and
the tubular member having an interior space that communicates with the cylindrical space, and
the concentration step comprises:
an aqueous dispersion-supplying step of supplying the aqueous dispersion into the cylindrical member inlet, and
a concentrated dispersion-recovering step of recovering a microcapsule dispersion discharged through the conical member outlet.

[3] The method according to [2], further comprising a dilute dispersion-recovering step of recovering a microcapsule dispersion having a microcapsule concentration lower than the microcapsule concentration in the microcapsule dispersion resulting from the concentrated dispersion-recovering step.

[4] The method according to [3],
wherein
the cyclone further comprises a midway outlet provided at a position that is closer to the tubular member outlet than the cylindrical member inlet is to the tubular member outlet and closer to the cylindrical member inlet than the tubular member outlet is to the cylindrical member inlet, and
the dilute dispersion-recovering step comprises a step of recovering a microcapsule dispersion discharged through the midway outlet.

[5] The method according to any one of [2] to [4],
wherein
the cyclone further comprises a relaxation member connected to the conical member, defining a flow-in space into which the microcapsule dispersion discharged through the conical member outlet flows, and relaxing the strength with which the microcapsule dispersion is discharged, and
the concentrated dispersion-recovering step comprises:
a flow-in step in which the microcapsule dispersion flows out of the conical space into the flow-in space and, at the time of discharge through the conical member outlet, the microcapsule dispersion receives pressure that is higher than the atmospheric pressure outside the relaxation member, and
a discharge step of discharging the microcapsule dispersion within the relaxation member out from the relaxation member.

[6] The method according to any one of [1] to [5], further comprising a step of lyophilizing the microcapsule dispersion resulting from the concentration step.

[7] The method according to any one of [1] to [6], wherein the microcapsule contains a physiologically active substance.

[8] The method according to [7], wherein the physiologically active substance is leuprorelin or a salt thereof.

For the purpose of achieving the object described above, the method for producing a microcapsule powder according to an embodiment of the present invention comprises a concentration step S92. In the concentration step S92, an aqueous dispersion of a microcapsule is supplied into a cyclone 10 and the aqueous dispersion is then concentrated.

The cyclone 10 desirably comprises a cylindrical member 20, a conical member 22, and a tubular member 24. The cylindrical member 20 comprises a cylindrical member inlet 40. The cylindrical member 20 defines a cylindrical space 30. The conical member 22 is attached to one end of the cylindrical member 20. The conical member 22 defines a conical space 32. The conical member 22 comprises a conical member outlet 50. The tubular member 24 is attached to the other end of the cylindrical member 20. The tubular member 24 comprises a tubular member outlet 66. The conical space 32 communicates with the cylindrical space 30. Interior spaces 70 and 72 of the tubular member 24 communicate with the cylindrical space 30. The concentration step S92 comprises an aqueous dispersion-supplying step S100 and a concentrated dispersion-recovering step S102. In the aqueous dispersion-supplying step S100, the aqueous dispersion is supplied into the cylindrical member inlet 40. In the concentrated dispersion-recovering step S102, a microcapsule dispersion having a microcapsule concentration that is higher than the microcapsule concentration in that aqueous dispersion of a microcapsule is recovered. This microcapsule dispersion is discharged through the conical member outlet 50.

Use of the cyclone 10 for concentrating an aqueous dispersion can easily reduce the time required for liquid component removal from an aqueous dispersion compared to use of a disc centrifuge for liquid component removal from an aqueous dispersion. The reason why the time can be easily reduced is the low ratio of liquid component removal compared to the case when a disc centrifuge is used for liquid component removal from an aqueous dispersion. As a result, productivity in separating a microcapsule from a liquid can be enhanced. In addition, use of the cyclone 10 for concentrating an aqueous dispersion does not require manual recovery of a microcapsule. This is because concentrating an aqueous dispersion by the cyclone 10 ensures the capability of the microcapsule dispersion to flow. The reason why the microcapsule dispersion thus can flow is the low ratio of liquid component removal compared to the case when a disc centrifuge is used for liquid component removal from an aqueous dispersion. When a disc centrifuge is used for liquid component removal from an aqueous dispersion, however, manual recovery of a centrifuged microcapsule is necessary. When manual recovery of a microcapsule is unnecessary, the chances of an operator being exposed to a microcapsule are lower than when manual recovery of a microcapsule is necessary. As the chances are reduced, less labor is required for ensuring safety.

When a disc centrifuge is used for liquid component removal from an aqueous dispersion, the rate of centrifugation at the time of liquid component removal has an upper limit thereto so as to prevent an aqueous dispersion or a supernatant from spilling out of the rotor, and this makes it difficult to reduce the time required for liquid component removal. On the other hand, use of the cyclone 10 for concentrating an aqueous dispersion does not require an upper limit set to the rate of centrifugation and therefore the time required for liquid component removal can be reduced as needed.

The concentration step S92 may comprise a dilute dispersion-recovering step S104. In the dilute dispersion-recovering step S104, a microcapsule dispersion having a microcapsule concentration that is lower than the microcapsule concentration in that aqueous dispersion of a microcapsule is recovered.

It is desirable that the cyclone 10 further comprises a midway outlet 64. The midway outlet 64 is provided at a position that is closer to the tubular member outlet 66 than the cylindrical member inlet 40 is to the tubular member outlet 66 and closer to the cylindrical member inlet 40 than the tubular member outlet 66 is to the cylindrical member inlet 40. In this case, the dilute dispersion-recovering step S104 comprises the following step. The step is a step of recovering a microcapsule dispersion discharged through the midway outlet 64.

It is desirable that the cyclone 10 further comprises a relaxation member 26. The relaxation member 26 is connected to the conical member 22. The relaxation member 26 defines a flow-in space 34. Into the flow-in space 34, a microcapsule dispersion flows. This microcapsule dispersion is the one discharged through the conical member outlet 50. The relaxation member 26 relaxes the strength with which the microcapsule dispersion is discharged. In this case, the concentrated dispersion-recovering step S102 comprises a flow-in step S110 and a discharge step S112. In the flow-in step S110, the microcapsule dispersion flows out of the conical space 32 into the flow-in space 34. At the time of flowing in, the microcapsule dispersion being discharged from the conical member outlet 50 is under pressure that is higher than the atmospheric pressure outside the relaxation member 26. In the discharge step S112, the microcapsule dispersion within the relaxation member 26 is discharged out from the relaxation member 26.

When the pressure that the microcapsule dispersion being discharged from the conical member outlet 50 receives is higher than the atmospheric pressure outside the relaxation member 26, gushing of the microcapsule dispersion out of the conical member outlet 50 can be inhibited compared to the opposite case. The gushing thus can be inhibited and therefore a scattering of the microcapsule dispersion can be inhibited. The scattering thus can be inhibited and therefore the yield of microcapsule production can be enhanced compared to the case where the scattering cannot be inhibited. The yield thus can be enhanced and the time required for dispersion removal can be easily reduced, and therefore productivity in separating a microcapsule from a liquid can be enhanced.

It is desirable that the method for producing a microcapsule powder further comprises a lyophilization step S94. In the lyophilization step S94, the microcapsule dispersion resulting from the concentration step S92 is lyophilized.

In the concentration step S92, the cyclone 10 is thus used for concentrating the aqueous dispersion. This can increase the fluidity of the microcapsule dispersion at the start of the lyophilization step S94 compared to the case where a disc centrifuge is used for liquid component removal from an aqueous dispersion. Because of the high fluidity thus achieved, the microcapsule dispersion can be easily transferred to a lyophilizer to start the lyophilization step S94. Because the microcapsule dispersion can be easily transferred to a lyophilizer, productivity can be enhanced correspondingly. In the lyophilization step S94, a liquid component in the microcapsule dispersion is removed. This allows the liquid component to be removed at the completion of the lyophilization step S94 as in the case where a known method is used to produce a microcapsule powder. As a result, removal of the liquid component can be achieved as in the case where a known method is used to produce a microcapsule powder, productivity in separating a microcapsule from an aqueous dispersion can be enhanced, and labor required for ensuring safety can be reduced.

Effects of the Invention

According to the present invention, productivity in separating a microcapsule from an aqueous dispersion can be enhanced and labor required for ensuring safety can be reduced.

EMBODIMENTS OF THE INVENTION

Figure 1:
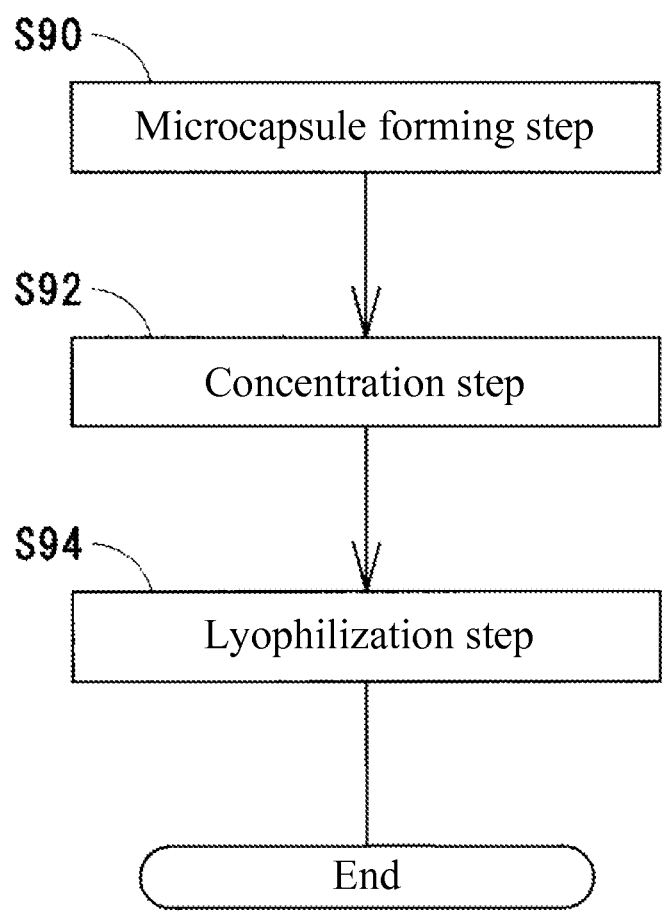
FIG. 1 shows steps in a method for producing a microcapsule powder according to an embodiment of the present invention.

Embodiments of the present invention are explained below referring to drawings. In the explanation below, the same members, parts, items, or the like are provided with the same reference numeral, and those provided with the same reference numeral have the same name and the same functions. Therefore, an overlapping detailed explanation of those is omitted.

[Explanation of Method for Producing Microcapsule Powder]

FIG. 1 shows steps in a method for producing a microcapsule powder according to an embodiment of the present invention. The method for producing a microcapsule powder according to the embodiment of the present invention is explained below based on FIG. 1. The method for producing a microcapsule powder according to the embodiment of the present invention comprises a dispersion-producing step S90, a concentration step S92, and a lyophilization step S94.

The dispersion-producing step S90 is a step of producing a liquid in which a microcapsule is dispersed in water (the water may contain an emulsifier described below) (in the explanation below, the liquid in which a microcapsule is dispersed in water is sometimes called an "aqueous dispersion"). An example of the dispersion-producing step S90 is explained below. The specifics of the dispersion-producing step S90, however, are not limited to the scope of the following example.

A microcapsule used in the present invention is produced by in-water drying of, for example, (i) a W (internal aqueous phase)/O (oil phase)/W (external aqueous phase) emulsion resulting from emulsification of a W (internal aqueous phase)/O (oil phase) emulsion composed of an internal aqueous phase containing a physiologically active substance and an oil phase containing a lactic acid polymer or a salt thereof or a lactic acid-glycolic acid copolymer or a salt thereof, or (ii) an O (oil phase)/W (external aqueous phase) emulsion resulting from emulsification of an oil phase containing a physiologically active substance and a lactic acid polymer or a salt thereof or a lactic acid-glycolic acid copolymer or a salt thereof. In the present invention, a microcapsule obtained by such in-water drying using no physiologically active substance can also be used. However, the microcapsule used in the present invention preferably contains a physiologically active substance.

The W/O emulsion (i) composed of an internal aqueous phase containing a physiologically active substance and an oil phase containing a lactic acid polymer or a salt thereof or a lactic acid-glycolic acid copolymer or a salt thereof is produced as follows.

First, a physiologically active substance is dissolved, dispersed, or suspended in water to give an internal aqueous phase. The concentration of the physiologically active substance in water is 0.001 to 90% (w/w), for example, and preferably 0.01 to 80% (w/w).

The amount of the physiologically active substance used varies depending on the kind, the desired pharmacological effect, the duration of the effect, and the like of the physiologically active substance and is about 0.01 to about 50% (w/w), for example, preferably about 0.1 to about 30% (w/w), and further preferably about 1 to about 20% (w/w), relative to the amount of the lactic acid polymer or the salt thereof or the lactic acid-glycolic acid copolymer or the salt thereof.

In order to increase the content of the physiologically active substance in the microcapsule, if necessary, a drug-retaining substance such as gelatin, agar-agar, sodium alginate, polyvinyl alcohol, and basic amino acids (arginine, histidine, and lysine, for example) may be added to the internal aqueous phase. The amount of the drug-retaining substance to be added is usually about 0.01 times to about 10 times the weight of the physiologically active substance.

Prior to use, the internal aqueous phase may be lyophilized so as to give a powder thereof and then dissolved in water to achieve an appropriate concentration.

Separately, a lactic acid polymer or a salt thereof or a lactic acid-glycolic acid copolymer or a salt thereof is dissolved in an organic solvent to give an oil phase.

Examples of the organic solvent comprise halogenated hydrocarbons (dichloromethane, chloroform, chloroethane, trichloroethane, and carbon tetrachloride, for example), fatty acid esters (ethyl acetate and butyl acetate, for example), and aromatic hydrocarbons (benzene, toluene, and xylene, for example), and preferable among these is dichloromethane.

The concentration of the lactic acid polymer or the salt thereof or the lactic acid-glycolic acid copolymer or the salt thereof in the organic solvent varies depending on the kind and the weight average molecular weight of the lactic acid polymer or the salt thereof or the lactic acid-glycolic acid copolymer or the salt thereof and the kind of the organic solvent, and is usually about 0.01 to about 90% (w/w) and preferably about 0.01 to about 70% (w/w) in terms of [weight of lactic acid polymer or salt thereof or lactic acid-glycolic acid copolymer or salt thereof/(weight of organic solvent+weight of lactic acid polymer or salt thereof or lactic acid-glycolic acid copolymer or salt thereof)] (×100%). The oil phase desirably contains no insoluble matter.

To the organic solvent solution of the lactic acid polymer or the salt thereof or the lactic acid-glycolic acid copolymer or the salt thereof (oil phase) thus obtained, the solution, the dispersion, or the suspension of the physiologically active substance in water (internal aqueous phase) is added, followed by dispersion by a homomixer or the like for emulsification to give a W/O emulsion.

When the production of the W/O emulsion is carried out at room temperature (about 19 to 25° C.), the resulting W/O emulsion can change over time to assume morphology unpreferable for secondary emulsification described below (gelled, for example) to make it difficult to achieve a high yield in microcapsule production (the yield herein refers to the proportion of the weight of the physiologically active substance in the microcapsule to the weight of the physiologically active substance in the W/O emulsion).

The oil phase (ii) containing a physiologically active substance and a lactic acid polymer or a salt thereof or a lactic acid-glycolic acid copolymer or a salt thereof is produced as follows.

First, an organic solvent solution of a lactic acid polymer or a salt thereof or a lactic acid-glycolic acid copolymer or a salt thereof is produced. The organic solvent used is the same organic solvent used in the production of the W/O emulsion.

The concentration of the lactic acid polymer or the salt thereof or the lactic acid-glycolic acid copolymer or the salt thereof in the organic solvent solution varies depending on the kind and the weight average molecular weight of the lactic acid polymer or the salt thereof or the lactic acid-glycolic acid copolymer or the salt thereof and the kind of the organic solvent, and is usually about 0.01 to about 70% (w/w) and preferably about 1 to about 60% (w/w) in terms of [weight of lactic acid polymer or salt thereof or lactic acid-glycolic acid copolymer or salt thereof/(weight of organic solvent+weight of lactic acid polymer or salt thereof or lactic acid-glycolic acid copolymer or salt thereof)](× 100%).

Then, a physiologically active substance is dissolved or suspended in the organic solvent solution of the lactic acid polymer or the salt thereof or the lactic acid-glycolic acid copolymer or the salt thereof to give an oil phase. The oil phase can also be produced by dissolving or suspending a solution in which a physiologically active substance is dissolved in an alcohol, in the organic solvent solution of the lactic acid polymer or the salt thereof or the lactic acid-glycolic acid copolymer or the salt thereof. Examples of the alcohol to dissolve the physiologically active substance comprise methanol.

The amount of the physiologically active substance used may be selected so as to give the same proportion of the physiologically active substance to the lactic acid polymer or the salt thereof as the proportion in the production of the W/O emulsion (i).

The W/O emulsion (i) or the oil phase (ii) is then added to an external aqueous phase, followed by dispersion by a homomixer or the like for emulsification (secondary emulsification) to give a corresponding emulsion (hereinafter, an emulsion obtained from the W/O emulsion is sometimes called a W/O/W emulsion, and an emulsion obtained from the oil phase (ii) is sometimes called an O/W emulsion).

The amount of the external aqueous phase used is usually about 1 to about 10,000 times, preferably about 10 to about 5,000 times, and particularly preferably about 50 to about 1,000 times the volume of the W/O emulsion or the oil phase.

To the external aqueous phase, an emulsifier is usually added. The emulsifier has only to be one generally capable of forming a stable W/O/W emulsion or a stable O/W emulsion. Examples thereof comprise anionic surfactants, nonionic surfactants, polyoxyethylene castor oil derivatives, polyvinylpyrrolidone, polyvinyl alcohol, carboxymethylcellulose, lecithin, gelatin, and hyaluronic acid, and preferable among these is polyvinyl alcohol. The concentration of the emulsifier in the external aqueous phase is usually about 0.001 to about 20% (w/w), preferably about 0.01 to about 10% (w/w), and particularly preferably about 0.05 to about 5% (w/w).

By subjecting the W/O/W emulsion or the O/W emulsion thus obtained (hereinafter, these are sometimes simply called emulsions for short) to in-water drying, the organic solvent in the emulsion can be removed to give an aqueous dispersion of a microcapsule.

Removal of the organic solvent may be followed, when needed, by sieving, separation of a microcapsule by a centrifuge, lyophilization, and dispersion of the resulting microcapsule powder together with an emulsifier in water, so as to use the resulting liquid as an aqueous dispersion of a microcapsule.

Instead of employing the method using a W/O/W emulsion or an O/W emulsion, the production can be carried out by in-water drying of an S (solid phase)/O (oil phase) emulsion composed of a solid phase containing a physiologically active substance and an oil phase containing a lactic acid polymer or a salt thereof or a lactic acid-glycolic acid copolymer or a salt thereof.

First, a lactic acid polymer or a salt thereof or a lactic acid-glycolic acid copolymer or a salt thereof is dissolved in an organic solvent, and to the resulting organic solvent solution, a physiologically active substance is dispersed. The amounts of the physiologically active substance and the lactic acid polymer or the salt thereof used in this case may be selected so as to give the same proportion of the physiologically active substance to the lactic acid polymer or the salt thereof or the lactic acid-glycolic acid copolymer or the salt thereof as the proportion in the production of the W/O emulsion (i). In order to achieve uniform dispersion of the physiologically active substance in the organic solvent solution, ultrasonic irradiation, a turbine stirrer, a homogenizer, and/or the like are used, for example.

The S/O emulsion thus prepared is then added to an external aqueous phase, followed by dispersion, for example, by ultrasonic irradiation, a turbine stirrer, a homogenizer, or the like, for emulsification to give an emulsion (hereinafter, sometimes called an S (solid phase)/O (oil phase)/W (aqueous phase) emulsion). Subsequently, the solvent in the oil phase is evaporated to give a microcapsule. The volume of the external aqueous phase in this case is selected generally from the range of about 1 time to about 10,000 times the volume of the oil phase, further preferably from the range of about 10 times to about 5,000 times, and particularly preferably from the range of about 50 times to about 1,000 times.

To the external aqueous phase, the emulsifier may be added. The amount of the external aqueous phase used and the kind and the concentration of the emulsifier added to the external aqueous phase are the same as those in the production of the W/O/W emulsion. By subjecting the S/O/W emulsion thus obtained to in-water drying to remove the organic solvent, an aqueous dispersion of a microcapsule can be obtained.

The aqueous dispersion containing a microcapsule thus obtained can be subjected to the concentration step S92, or can be sieved and then subjected to the concentration step S92.

The "physiologically active substance" according to the embodiment of the present invention refers to a substance comprised within the microcapsule and having physiological activity.

The physiologically active substance used in the present invention is not particularly limited provided that it is pharmacologically useful, and may be either a non-peptide compound or a peptide compound. Examples of the non-peptide compound comprise agonists, antagonists, and compounds having inhibitory action on enzymes. The peptide compound is preferably a physiologically active peptide, for example, and is preferably a physiologically active peptide with a molecular weight of about 300 to about 40,000, preferably about 400 to about 30,000, and further preferably about 500 to about 20,000.

Examples of the physiologically active peptide comprise luteinizing hormone-releasing hormone (LH-RH), insulin, somatostatin, somatotropin, growth hormone-releasing hormone (GH-RH), prolactin, erythropoietin, adrenal cortical hormones, melanocyte-stimulating hormones, thyroid hormone-releasing hormone, thyroid-stimulating hormone, luteinizing hormone, follicle-stimulating hormone, vasopressin, oxytocin, calcitonin, gastrin, secretin, pancreozymin, cholecystokinin, angiotensin, human placental lactogen, human chorionic gonadotropin, enkephalin, endorphin, kyotorphin, tuftsin, thymopoietin, thymosin, thymothymulin, thymic humoral factors, serum thymic factors, tumor necrosis factors, colony-stimulating factors, motilin, dynorphin, bombesin, neurotensin, caerulein, bradykinin, atrial natriuretic factors, nerve growth factors, cell growth factors, neurotrophic factors, and peptides having endothelin antagonist action, and derivatives thereof, and the fragments or derivatives of the fragments of these.

The physiologically active substance may be used as it is or as a pharmaceutically acceptable salt thereof. Examples of such a salt comprise, in the case where the physiologically active substance has a basic group such as an amino group, salts thereof with an inorganic acid (sometimes called an inorganic free acid) or an organic acid (sometimes called an organic free acid). Examples of the inorganic acid comprise carbonic acid, bicarbonic acid, hydrochloric acid, sulfuric acid, nitric acid, and boric acid. Examples of the organic acid comprise succinic acid, acetic acid, propionic acid, and trifluoroacetic acid.

Examples of the salt of the physiologically active substance comprise, in the case where the physiologically active substance has an acidic group such as a carboxy group, salts thereof with an inorganic base (sometimes called an inorganic free base), an organic base (sometimes called an organic free base), or the like. Examples of the inorganic base comprise alkali metals such as sodium and potassium and alkaline-earth metals such as calcium and magnesium. Examples of the organic base comprise organic amines such as triethylamine and basic amino acids such as arginine.

The physiologically active peptide may be in the form of a metal complex compound (a copper complex or a zinc complex, for example). Preferable examples of the physiologically active peptide comprise LH-RH derivatives or salts thereof effective in hormone-dependent diseases, in particular sex hormone-dependent diseases such as sex hormone-dependent cancers (prostate cancer, uterine cancer, breast cancer, and pituitary tumors, for example), prostatic hyperplasia, endometriosis, uterine fibroids, precocious puberty, dysmenorrhea, amenorrhea, premenstrual syndrome, and polycystic ovary syndrome, and contraception (or infertility when taking advantage of rebound effects after a drug holiday). In addition, LH-RH derivatives or salts thereof effective in benign and malignant tumors and the like that are sex hormone-independent and responsive to LH-RH are also exemplified.

Specific examples of the LH-RH derivatives or salts thereof comprise peptides described in Treatment with GnRH analogs: Controversies and perspectives [issued by The Parthenon Publishing Group, Ltd. in 1996], Japanese Translation of PCT Publication No. 3-503165, Japanese Patent Application Laid-open No. 3-101695, Japanese Patent Application Laid-open No. 7-97334, Japanese Patent Application Laid-open No. 8-259460, and the like.

Examples of the LH-RH derivatives comprise LH-RH agonists and LH-RH antagonists. For example, the LH-RH antagonist used is degarelix or cetrorelix or a salt thereof (an acetate thereof, for example).

Examples of the LH-RH agonists comprise physiologically active peptides of formula [II]:

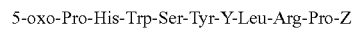

5-oxo-Pro-His-Trp-Ser-Tyr-Y-Leu-Arg-Pro-Z

[where Y is a residue selected from DLeu, DAla, DTrp, DSer (tBu), D2Mal, and DHis (ImBzl), and Z is NH—$C_2H_5$ or Gly-$NH_2$], and salts thereof. Particularly preferable as the LH-RH agonist is such a peptide in which Y is DLeu and Z is NH—$C_2H_5$ (in other words, a peptide of 5-oxo-Pro-His-Trp-Ser-Tyr-Dleu-Leu-Arg-Pro-NH—$C_2H_5$; leuprorelin) or a salt thereof (an acetate thereof, for example) (in the present specification, leuprorelin acetate is sometimes called a compound B).

The physiologically active substance is preferably leuprorelin or a salt thereof, further preferably leuprorelin or an acetate thereof, and particularly preferably leuprorelin acetate.

Preferable examples of the physiologically active substance comprise Ac-D-Tyr-Hyp-Asn-Thr-Phe-AzaGly-Leu-Arg(Me)-Trp-$NH_2$ described in WO 2007/072997 (compound number 723) or a salt thereof (preferably an acetate thereof). Especially preferable is the compound number 723 in an acetate form (in the present specification, sometimes called a compound A).

The lactic acid polymer in the present specification refers to a polymer solely composed of lactic acid.

The weight average molecular weight of the lactic acid polymer or the salt thereof used in the present specification is about 5,000 to about 40,000, preferably about 5,000 to about 30,000, and further preferably about 6,000 to about 20,000.

The dispersity (weight average molecular weight/number average molecular weight) of the lactic acid polymer or the salt thereof is preferably about 1.2 to about 4.0 and further preferably about 1.5 to about 3.5.

As the lactic acid polymer or the salt thereof, a commercially available product can also be used.

The lactic acid-glycolic acid copolymer or a salt thereof in the present specification refers to a polymer composed of lactic acid and glycolic acid, or a salt thereof. The content of glycolic acid in the lactic acid-glycolic acid copolymer used in the present specification is higher than 0% by weight and not higher than about 60% by weight, preferably not lower than 1% by weight and not higher than 55% by weight, more preferably not lower than 5% by weight and not higher than about 50% by weight, further preferably not lower than about 15% and not higher than about 35%, and particularly preferably about 25% by weight.

The weight average molecular weight of the lactic acid-glycolic acid copolymer used in the present specification is about 5,000 to about 40,000, preferably about 5,000 to about 30,000, and further preferably about 6,000 to about 20,000.

The dispersity (weight average molecular weight/number average molecular weight) of the lactic acid-glycolic acid copolymer is preferably about 1.2 to about 4.0 and further preferably about 1.5 to about 3.5.

As the lactic acid-glycolic acid copolymer, a commercially available product can also be used.

The weight average molecular weight and the dispersity in the present specification refer to the values measured by gel permeation chromatography (GPC). For example, the weight average molecular weight and the content of each polymer are a weight average molecular weight in terms of polystyrene measured by GPC using monodisperse polystyrene as a reference material and the content of each polymer determined therefrom by calculation, respectively. Measurement of the weight average molecular weight and the content of each polymer can be performed, for example, on a high-performance GPC device (manufactured by Tosoh Corporation; HLC-8120GPC). As a column, SuperH4000×2 and SuperH2000 (either of these is manufactured by Tosoh Corporation) can be used. Tetrahydrofuran can be used as the mobile phase, and the flow speed can be set at 0.6 mL/min. For detection, a differential refractive index can be used.

After the dispersion-producing step S90, the concentration step S92 is carried out by an operator. The concentration step S92 is a step of supplying the aqueous dispersion into a cyclone 10 and then concentrating the aqueous dispersion. The specifics of the concentration step S92 are to be described.

After the concentration step S92, the lyophilization step S94 is carried out. The lyophilization step S94 is a step of lyophilizing the liquid resulting from the concentration step S92 by a well-known lyophilizer. In this step, moisture is removed from the microcapsule dispersion. The difference between a well-known lyophilization step and the lyophilization step S94 according to the embodiment of the present invention is the water content in the matter that is to be subjected to freezing and drying. In a well-known lyophilization step, the matter that is to be subjected to freezing and drying is a microcapsule from which most moisture has been removed by a centrifuge or a filtration device, while in the lyophilization step S94 according to the embodiment of the present invention, the matter that is to be subjected to freezing and drying is a microcapsule dispersion. The microcapsule dispersion contains moisture in large quantity compared to a microcapsule from which most moisture has been removed by a centrifuge or a filtration device. In the other aspects, the lyophilization step S94 according to the embodiment of the present invention is the same as a well-known lyophilization step, and therefore detailed explanation thereof is omitted here.

[Explanation of Cyclone]

Figure 2:
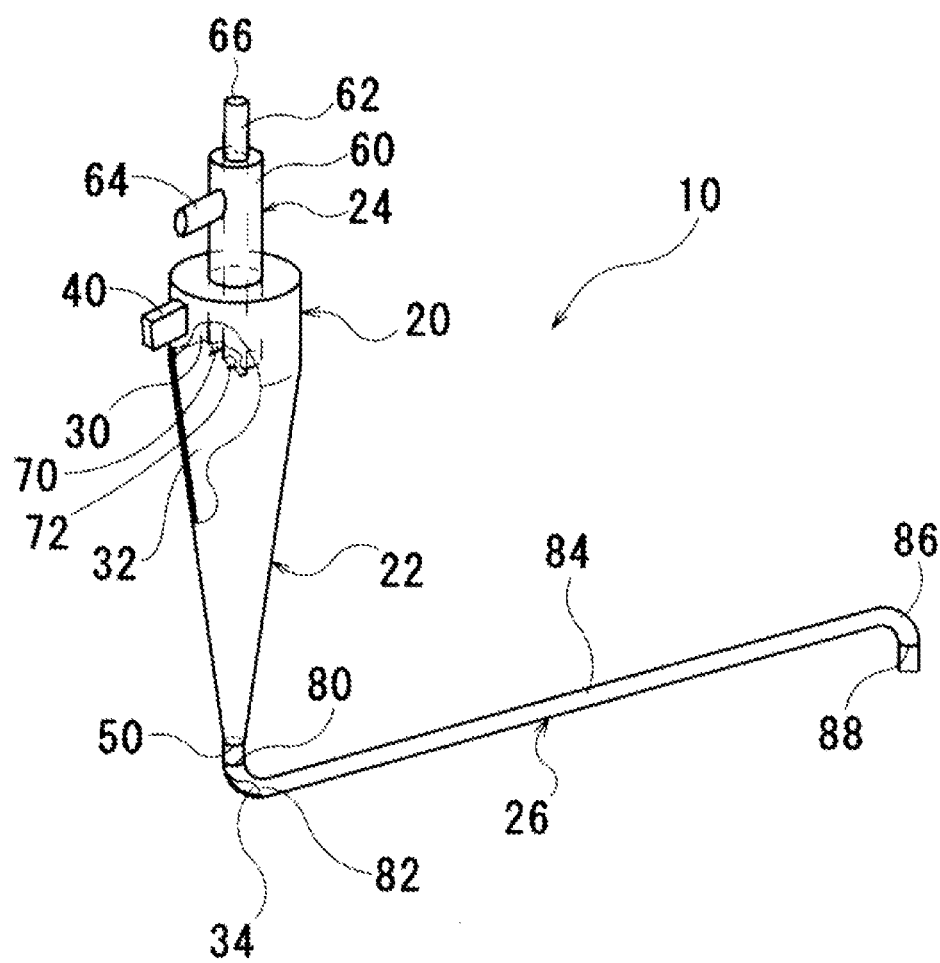
FIG. 2 shows the structure of a cyclone according to an embodiment of the present invention.

FIG. 2 shows the structure of the cyclone 10 according to the embodiment of the present invention. FIG. 2 is a partially cutaway view of the cyclone 10. Prior to explanation of the specifics of the concentration step S92, the configuration of the cyclone 10 according to the embodiment of the present invention is explained below based on FIG. 2.

The material of the cyclone 10 according to the embodiment of the present invention is preferably SUS304, SUS316, or SUS316L defined by Japan Industrial Standard. The material of the cyclone 10 according to the embodiment of the present invention is particularly preferably SUS316L. The cyclone 10 according to the embodiment of the present invention comprises a cylindrical member 20, a conical member 22, a tubular member 24, and a relaxation member 26. The cylindrical member 20 defines a cylindrical space 30. The cylindrical member 20 comprises a cylindrical member inlet 40. The conical member 22 is attached to one end of the cylindrical member 20. The cylindrical member 20 is integrated with the conical member 22. The conical member 22 defines a conical space 32. The conical space 32 communicates with the cylindrical space 30. The conical member 22 comprises a conical member outlet 50. The cyclone 10 according to the embodiment of the present invention may be accommodated within a casing (not shown). The shape and the structure of the casing are not directly related to the present invention, and therefore explanation of the shape and the structure of the casing is omitted.

The tubular member 24 is attached to the other end of the cylindrical member 20. The tubular member 24 comprises an outer tube 60 and an inner tube 62. The outer tube 60 and the inner tube 62 together form a double tube. The outer tube 60 comprises a midway outlet 64 provided on the side surface thereof. The outer tube 60 is closed at an end. The inner tube 62 comprises a tubular member outlet 66 provided at an end thereof. The midway outlet 64 is provided at a position that is closer to the tubular member outlet 66 than the cylindrical member inlet 40 is to the tubular member outlet 66. In other words, the distance between the tubular member outlet 66 and the midway outlet 64 is shorter than the distance between the tubular member outlet 66 and the cylindrical member inlet 40. The midway outlet 64 is provided at a position that is closer to the cylindrical member inlet 40 than the tubular member outlet 66 is to the cylindrical member inlet 40. In other words, the distance between the cylindrical member inlet 40 and the midway outlet 64 is shorter than the distance between the cylindrical member inlet 40 and the tubular member outlet 66. The outer tube 60 comprises an interior space 70 that communicates with the cylindrical space 30 and the conical space 32. The inner tube 62 comprises an interior space 72 that communicates with the cylindrical space 30 and the conical space 32.

The inner diameter of the tubular member outlet is preferably 0.1 to 3.0 mm, more preferably 1.5 to 2.5 mm, and further preferably 2.0 mm.

The relaxation member 26 is connected to the conical member 22. The relaxation member 26 defines a flow-in space 34. Into the flow-in space 34, the microcapsule dispersion flows. The microcapsule dispersion is discharged through the conical member outlet 50. The relaxation member 26 relaxes the strength with which the microcapsule dispersion is discharged.

The inner diameter of the conical member outlet is preferably 0.1 to 2.5 mm, more preferably 1.0 to 2.0 mm, and further preferably 1.5 mm.

In the embodiment of the present invention, the relaxation member 26 comprises a flow-in port 80, a bend 82 on the flow-in side, a straight tubular portion 84, a bend 86 on the flow-out side, and a concentrated dispersion flow-out port 88. The flow-in port 80 communicates with the conical member outlet 50 of the conical member 22. This allows the microcapsule dispersion to flow out of the conical space 32 into the flow-in space 34.

Each of the bend 82 on the flow-in side and the bend 86 on the flow-out side is a bended part of the relaxation member 26, and the presence of these gives the relaxation member 26 of the embodiment of the present invention a "Z"-shape. The presence of the bend 82 on the flow-in side and the bend 86 on the flow-out side applies resistance on the microcapsule dispersion that flows into the flow-in space 34. Due to the resistance thus applied, the strength with which the microcapsule dispersion flows into the flow-in space 34 is relaxed. The straight tubular portion 84 is a straight part between the bend 82 on the flow-in side and the bend 86 on the flow-out side.

[Explanation of Concentration Step]

Figure 3:
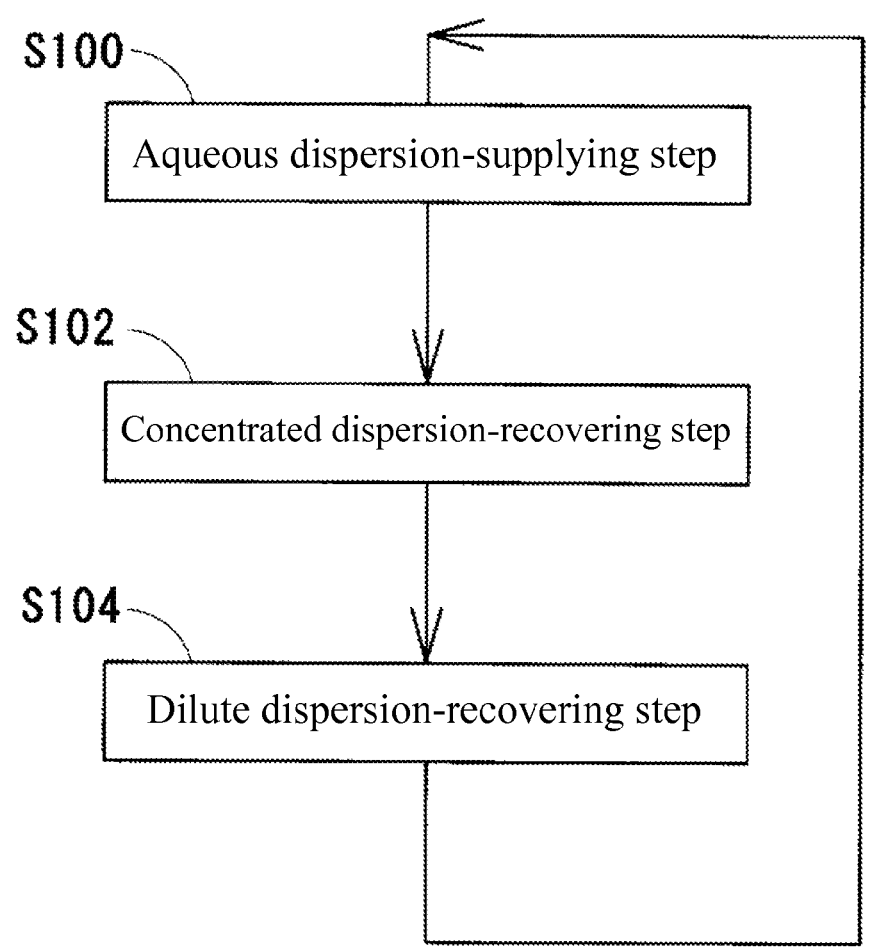
FIG. 3 shows the specifics of a concentration step according to an embodiment of the present invention.

FIG. 3 shows the specifics of a concentration step S92 according to an embodiment of the present invention. The concentration step S92 according to the embodiment of the present invention is explained below based on FIG. 2 and FIG. 3. The concentration step S92 according to the embodiment of the present invention comprises an aqueous dispersion-supplying step S100, a concentrated dispersion-recovering step S102, and a dilute dispersion-recovering step S104.

The aqueous dispersion-supplying step S100 is carried out first. The aqueous dispersion-supplying step S100 is a step of supplying an aqueous dispersion into a cylindrical member inlet 40 of a cyclone 10. The aqueous dispersion is supplied into the cylindrical member inlet 40 by a well-known pump or compressed air or nitrogen.

The pump pressure at the time of supplying is preferably 0.3 to 1.5 MPa, more preferably 0.5 to 1.0 MPa, and further preferably 0.8 MPa.

After the aqueous dispersion-supplying step S100, the concentrated dispersion-recovering step S102 is carried out. The concentrated dispersion-recovering step S102 is a step of recovering a microcapsule dispersion discharged through a conical member outlet 50. As a result, a "concentrated dispersion" according to the embodiment of the present invention is obtained. The specifics of the concentrated dispersion-recovering step S102 are to be described.

After the concentrated dispersion-recovering step S102, the dilute dispersion-recovering step S104 is carried out. The dilute dispersion-recovering step S104 is a step of recovering a microcapsule dispersion having a microcapsule concentration lower than the microcapsule concentration in the concentrated dispersion. As a result, a "dilute dispersion" according to the embodiment of the present invention is obtained. The specifics of the dilute dispersion-recovering step S104 are to be described.

[Explanation of Concentrated Dispersion-Recovering Step]

Figure 4:
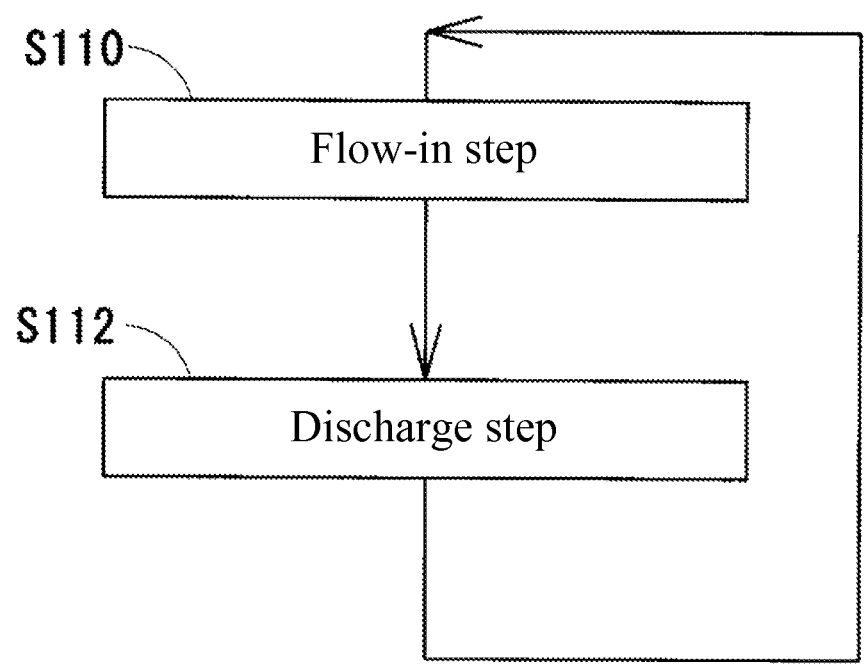
FIG. 4 shows the specifics of a concentrated dispersion-recovering step according to an embodiment of the present invention.

FIG. 4 shows the specifics of a concentrated dispersion-recovering step S102 according to an embodiment of the present invention. The concentrated dispersion-recovering step S102 according to the embodiment of the present invention is explained below based on FIG. 2 and FIG. 4. The concentrated dispersion-recovering step S102 according to the embodiment of the present invention comprises a flow-in step S110 and a discharge step S112.

The flow-in step S110 is carried out first. The flow-in step S110 is a step in which a concentrated dispersion flows out of a conical space 32 into a flow-in space 34. In the embodiment of the present invention, this step is carried out automatically following an aqueous dispersion-supplying step S100. In order to achieve this, a conical member outlet 50 is connected to a flow-in port 80 by a short straight tube in advance. The pressure that the concentrated dispersion receives within a cyclone 10 is higher than the atmospheric pressure in a relaxation member 26 (the atmospheric pressure in the flow-in space 34). Because of this, the concentrated dispersion gushes out of the conical member outlet 50 when the concentrated dispersion flows out of the conical space 32 into the flow-in space 34. The concentrated dispersion that has gushed out of the conical member outlet 50 receives resistance within the flow-in space 34. Due to the resistance thus applied, the pressure that the concentrated dispersion discharged through the conical member outlet 50 receives is higher than the atmospheric pressure outside the relaxation member 26. When the pressure that the concentrated dispersion receives is higher than the atmospheric pressure outside the relaxation member 26, the strength with which the concentrated dispersion is discharged is relaxed compared to the opposite case.

After the flow-in step S110, the discharge step S112 is carried out. The discharge step S112 is a step of discharging the concentrated dispersion in the relaxation member 26 (the flow-in space 34) out from the relaxation member 26. In the embodiment of the present invention, this step is carried out automatically following the flow-in step S110. In order to achieve this, a container (not shown) is placed in advance in the downstream side of the relaxation member 26. The strength with which the concentrated dispersion is discharged is already relaxed and therefore gushing of the concentrated dispersion out from the relaxation member 26 is inhibited.

[Explanation of Dilute Dispersion-Recovering Step]

Figure 5:
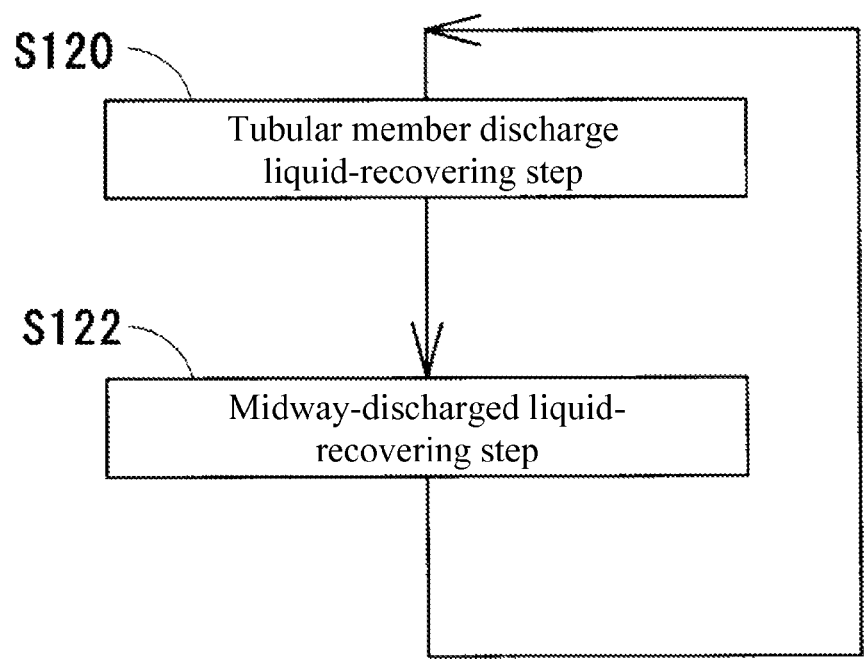
FIG. 5 shows the specifics of a dilute dispersion-recovering step according to an embodiment of the present invention.

FIG. 5 shows the specifics of a dilute dispersion-recovering step S104 according to an embodiment of the present invention. The dilute dispersion-recovering step S104 according to the embodiment of the present invention is explained below based on FIG. 4 and FIG. 5. The dilute dispersion-recovering step S104 according to the embodiment of the present invention comprises a tubular member discharge liquid-recovering step S120 and a midway discharged liquid-recovering step S122.

The tubular member discharge liquid-recovering step S120 is carried out first. The tubular member discharge liquid-recovering step S120 is a step of recovering a microcapsule dispersion discharged through a tubular member outlet 66. This microcapsule dispersion is a "tubular member discharge liquid" according to the embodiment of the present invention. The tubular member discharge liquid has a microcapsule concentration lower than the microcapsule concentration in an aqueous dispersion of a microcapsule supplied into a cylindrical member inlet 40. The specific method to recover the tubular member discharge liquid is not particularly limited, and may be placement of a well-known container, for example.

Then, the midway discharged liquid-recovering step S122 is carried out. The midway discharged liquid-recovering step S122 is a step of recovering a microcapsule dispersion discharged through a midway outlet 64. This microcapsule dispersion is a "midway-discharged liquid" according to the embodiment of the present invention. The midway-discharged liquid has a microcapsule concentration lower than the microcapsule concentration in the concentrated dispersion. The specific method to recover the midway-discharged liquid is not particularly limited, and may also be placement of a well-known container as in the tubular member discharge liquid-recovering step S120, for example. Although FIG. 5 shows that the midway discharged liquid-recovering step S122 is carried out after the tubular member discharge liquid-recovering step S120, the midway discharged liquid-recovering step S122 may be carried out before the tubular member discharge liquid-recovering step S120. Alternatively, the tubular member discharge liquid-recovering step S120 and the midway discharged liquid-recovering step S122 may be carried out in parallel.

[Explanation of Modifications]

The embodiments disclosed herein are examples in all aspects. The scope of the present invention is not limited based on the embodiments described above and, needless to mention, various modifications may be made on the configuration without departing from the purport of the present invention.

For example, the method for producing a microcapsule powder according to the present invention may comprise a step, different from the lyophilization step S94, to remove moisture from a concentrated dispersion.

In the method for producing a microcapsule powder according to the present invention, the structure of the relaxation member 26 is not limited to the structure described above. For example, instead of the relaxation member 26 described above, a tube having a well-known accumulator may be used as a relaxation member. If emphasis is not placed on the problem of scattering of a concentrated dispersion, the cyclone 10 may not necessarily have the relaxation member 26. When the relaxation member 26 is not provided, the microcapsule dispersion flowed out of the conical space 32 may be received by a certain container. The microcapsule dispersion received by the container may be lyophilized in the lyophilization step S94.

The shape of the conical member 22 may not necessarily be exactly conical. For example, the conical member may assume a shape that is similar to a frustum (a shape of a cone the pointed part of which is cut off to form a plane). In this case, the flat portion on top of the frustum may be provided with an outlet through which the concentrated dispersion is discharged.

In the method for producing a microcapsule powder of the present invention, a microcapsule with a very small particle diameter (5 μm or smaller, for example) is preferably removed in the concentration step. Due to the removal of a microcapsule with a very small particle diameter (5 μm or smaller, for example), the average particle diameter based on the number of microcapsules and the average particle diameter based on the volume thereof increase, an excessive release of a physiologically active substance from a microcapsule in an early stage is inhibited, and a prolonged and consistent release of a physiologically active substance from a microcapsule is achieved. For removal of a microcapsule with a very small particle diameter, the cyclone 10 to which the tubular member outlet 66 is provided is suitable.

The cyclone used in the present invention may have a structure that is different from the structure shown in FIG. 2. For example, a cyclone that comprises a cylindrical tube installed instead of a tubular member 24 and, except for this aspect, has the same structure as that of the cyclone 10 shown in FIG. 2 (hereinafter, this cyclone is sometimes called a "two-liquid classification cyclone") may be used in the present invention. When a two-liquid classification cyclone is used, the inner diameter of its part corresponding to the tubular member outlet 66 of the cyclone 10 shown in FIG. 2 (the inner diameter of the tube installed instead of a tubular member 24) is preferably 0.1 to 10.0 mm, more preferably 5.0 to 7.0 mm, and further preferably 6.0 mm.

EXPLANATION OF EXAMPLES

Examples of the present invention are explained below. The present invention is, however, not limited to the following examples.

Example 1

In this example, a cyclone (not shown) having the same structure as that of the cyclone 10 described above was used. This cyclone, unlike the cyclone 10 shown in FIG. 2, was accommodated within a casing. The cyclone used in this example comprised a conical member outlet having an inner diameter of 1.0 mm. The cyclone comprised a midway outlet having an inner diameter of 6.0 mm. The cyclone comprised a tubular member outlet having an inner diameter of 2.0 mm. To the cyclone, a well-known pump was connected. The pressure at which the pump discharged fluid was 0.6 MPa.

The procedure of this example is explained below. First, 1932.0 g of acetic acid and 644.0 g of methanol were mixed to give an acetic acid-methanol mixture. Then, 2807.7 g of a lactic acid-glycolic acid copolymer (ratio L/G=75/25, weight average molecular weight: 10000, manufactured by Wako Pure Chemical Industries, Ltd.) was dissolved in 3864.0 g of dichloromethane to give a polymer solution. To 6671.7 g of the polymer solution, 2576.0 g of the acetic acid-methanol mixture was mixed to give an O phase. The O phase was then filtrated with a 0.2-μm filter (PHOBIC DURAPOREOPTICAXL5: Millipore Corporation). Subsequently, 8041.5 g of the O phase was injected into 200 liters (0.2 cubic meters) of a 0.1%-(w/w) aqueous polyvinyl alcohol (EG-40, manufactured by The Nippon Synthetic Chemical Industry Co., Ltd.) solution that had been adjusted to about 18° C. (291.15 K) in advance. The aqueous solution into which the O phase had thus been injected was subjected to secondary emulsification by a turbine homomixer (manufactured by Tokushu Kika Kogyo Co., Ltd.) (turbine rotational speed: about 7,000 rpm). As a result, an O/W emulsion was formed. The O/W emulsion was stirred for about 3 hours (in-water drying step), followed by sieving through a standard sieve of 75 micrometers. By this, microcapsules that did not pass through the standard sieve of 75 micrometers were removed from the O/W emulsion. After sieving, the O/W emulsion was supplied into a filter-cloth centrifuge (HC-130C custom-engineered by Kokusan Co., Ltd.) at a flow speed of 500 mL/min, whereby a microcapsule was recovered. To the recovered microcapsule liquid, 338.8 g of mannitol was added, and the resultant was lyophilized by a lyophilizes (DFM-05A-S custom-engineered by ULVAC, Inc.). As a result, a microcapsule powder was obtained. In 20 liters of a 0.1% aqueous polyvinyl alcohol (PVA) solution, 140 g (0.14 kg) of the microcapsule powder was dispersed to give an aqueous dispersion. The microcapsule concentration in the aqueous dispersion was about 6.0 g/liter (about 6 kg/cubic meter). Subsequent to the production of the aqueous dispersion, a concentration step S92 was carried out, where a microcapsule dispersion was recovered through a conical member outlet 50, a midway outlet 64, and a tubular member outlet 66. The microcapsule dispersion recovered through the conical member outlet 50 was a concentrated dispersion. The microcapsule dispersion recovered through the midway outlet 64 was a midway-discharged liquid. The microcapsule dispersion recovered through the tubular member outlet 66 was a tubular member discharge liquid. The midway-discharged liquid was automatically mixed with the aqueous dispersion (this mixing was achieved by the connection between the channel from the pump described above to the cyclone 10 and the channel in which the midway-discharged liquid traveled). The tubular member discharge liquid was discarded. Right after the completion of supplying the aqueous dispersion, about 2 liters (0.002 cubic meters) of distilled water was supplied into the cyclone 10 by the pump described above for rinsing. After supplying distilled water, the concentrated dispersion was supplied into the cyclone 10 by the pump described above. As a result, the concentrated dispersion was further concentrated. The liquid discharged through the midway outlet 64 as a result of this concentration was automatically mixed with the concentrated dispersion. After the concentrated dispersion thus concentrated was recovered, the concentrated dispersion thus concentrated was lyophilized by a well-known lyophilizer. The tubular member discharge liquid was lyophilized by a well-known lyophilizer.

Example 2

The cyclone used in this example was the same cyclone as used in Example 1. The cyclone used in this example, however, was different from the cyclone used in Example 1 in that the inner diameter of the tubular member outlet was 1.5 mm. In the other aspects, the cyclone used in this example was the same as the cyclone used in Example 1. The procedure was the same as in Example 1.

Example 3

The cyclone used in this example was the same cyclone as used in Example 1. The cyclone used in this example, however, was different from the cyclone used in Example 1 in that the inner diameter of the conical member outlet was 1.5 mm. In the other aspects, the cyclone used in this example was the same as the cyclone used in Example 1. The procedure was the same as in Example 1.

Example 4

The cyclone used in this example was the same cyclone as used in Example 1. The cyclone used in this example, however, was different from the cyclone used in Example 1 in that the inner diameter of the conical member outlet was 1.5 mm and the inner diameter of the tubular member outlet was 1.5 mm. In the other aspects, the cyclone used in this example was the same as the cyclone used in Example 1. The procedure was the same as in Example 1.

Example 5

The cyclone used in this example was the same cyclone as used in Example 1. To the cyclone used in this example, a well-known pump was connected. The pressure at which the pump discharged fluid was 0.8 MPa. In the other aspects, the cyclone used in this example was the same as the cyclone used in Example 1. The procedure was the same as in Example 1.

Example 6

The cyclone used in this example was the same cyclone as used in Example 1. The cyclone used in this example, however, was different from the cyclone used in Example 1 in that the inner diameter of the tubular member outlet was 1.5 mm and the pressure at which a well-known pump connected to the cyclone discharged fluid was 0.8 MPa. In the other aspects, the cyclone used in this example was the same as the cyclone used in Example 1. The procedure was the same as in Example 1.

Example 7

The cyclone used in this example was the same cyclone as used in Example 1. The cyclone used in this example, however, was different from the cyclone used in Example 1 in that the inner diameter of the conical member outlet was 1.5 mm, the inner diameter of the tubular member outlet was 2.0 mm, and the pressure at which a well-known pump connected to the cyclone discharged fluid was 0.8 MPa. In the other aspects, the cyclone used in this example was the same as the cyclone used in Example 1. The procedure was the same as in Example 1.

[Results of Experiment Related to Example 1 to Example 7]

The results of the experiment related to Example 1 to Example 7 are shown in Table 1. Table 1 shows the treatment rate of a cyclone (the flow rate of an aqueous dispersion being supplied into a cyclone), the average particle diameter of a microcapsule in a concentrated dispersion after concentration (concentrated liquid average particle diameter), the average particle diameter of a microcapsule in a tubular member discharge liquid (tubular member liquid average particle diameter), and the recovery rate. The recovery rate is: mass of microcapsule powder resulting from lyophilization/mass of microcapsule powder dispersed in 0.1% aqueous polyvinyl alcohol solution×100.

TABLE 1

| | Pump pressure | Inner diameter of conical member outlet | Inner diameter of tubular member outlet | Treatment rate | | Concentrated liquid average particle diameter | Tubular member liquid average particle diameter | Recovery rate |
|---|---|---|---|---|---|---|---|---|
| | MPa | mm | mm | L/min | m³/sec | μm | μm | rate % |
| Example 1 | 0.6 | 1.0 | 2.0 | 0.88 | $1.47 \times 10^{-5}$ | 22.9 | 5.3 | 72.2 |
| Example 2 | | 1.0 | 1.5 | 0.46 | $7.67 \times 10^{-6}$ | 19.4 | 4.9 | 86.7 |
| Example 3 | | 1.5 | 2.0 | 0.80 | $1.33 \times 10^{-5}$ | 24.1 | 4.5 | 72.9 |

TABLE 1-continued

|  | Pump pressure MPa | Inner diameter of conical member outlet mm | Inner diameter of tubular member outlet mm | Treatment rate | | Concentrated liquid average particle diameter μm | Tubular member liquid average particle diameter μm | Recovery rate % |
| --- | --- | --- | --- | --- | --- | --- | --- | --- |
|  |  |  |  | L/min | m³/sec |  |  |  |
| Example 4 |  | 1.5 | 1.5 | 0.48 | $8.00 \times 10^{-6}$ | 22.6 | 4.8 | 91.2 |
| Example 5 | 0.8 | 1.0 | 2.0 | 0.92 | $1.53 \times 10^{-5}$ | 21.5 | 5.1 | 76.3 |
| Example 6 |  | 1.0 | 1.5 | 0.42 | $7.00 \times 10^{-6}$ | 21.6 | 4.6 | 83.2 |
| Example 7 |  | 1.5 | 2.0 | 1.05 | $1.75 \times 10^{-5}$ | 25.5 | 4.8 | 86.3 |

Studies conducted on Examples 1 to 7 proved that, by appropriately selecting pump pressure, the inner diameter of a conical member outlet, and the inner diameter of a tubular member outlet, an aqueous dispersion of a microcapsule could be concentrated by a cyclone.

In particular, when pump pressure was 0.8 MPa, the inner diameter of a conical member outlet was 1.5 mm, and the inner diameter of a tubular member outlet was 2.0 mm, concentration was achieved at a high treatment rate and an excellent recovery rate.

Example 8

In this example, the same cyclone as in Example 7 was used. To this cyclone, the same pump as in Example 7 was connected.

The procedure of this example is explained below. In this experiment, 140 g of the microcapsule powder described in Example 1 was dispersed in 20 liters of a 0.1% aqueous polyvinyl alcohol (PVA) solution to give an aqueous dispersion of a microcapsule. The microcapsule concentration in the aqueous dispersion was about 6.0 g/liter (about 6 kg/cubic meters). The aqueous dispersion was subjected to a concentration step S92, where a microcapsule dispersion was recovered through a conical member outlet 50, a midway outlet 64, and a tubular member outlet 66. Every 1 minute (60 seconds), 10 milliliters (10 cubic micrometers) of a midway-discharged liquid was sampled. The rest of the midway-discharged liquid was automatically mixed with the aqueous dispersion in the same manner as in Example 1. A tubular member discharge liquid was discarded. The midway-discharged liquid thus sampled was lyophilized by a well-known lyophilizer.

[Results of Experiment Related to Example 8]

Results of the experiment related to Example 8 are shown in Table 2. Table 2 shows influence of the sampling time (in other words, duration of treatment by a cyclone) on the average particle diameter of a microcapsule in the midway-discharged liquid (midway-discharged liquid average particle diameter) and the dry mass of a microcapsule.

Results in Table 2 clearly show that the fluctuation in the midway-discharged liquid average particle diameter and the dry mass was small when the duration was 10 minutes (600 seconds) or longer.

Example 9

In this example, the same cyclone as in Example 7 was used. To this cyclone, the same pump as in Example 7 was connected.

The procedure of this example is explained below. An aqueous dispersion was produced, and then a concentration step S92 was carried out, where a microcapsule dispersion was recovered through a conical member outlet 50, a midway outlet 64, and a tubular member outlet 66. A midway-discharged liquid was automatically mixed with the aqueous dispersion in the same manner as in Example 1. A tubular member discharge liquid was discarded. Concentration of the aqueous dispersion was continued for 10 minutes (600 seconds). When 10 minutes (600 seconds) had passed in concentration, part of the midway-discharged liquid not yet mixed with the aqueous dispersion at that time was discarded. Right after the completion of supplying the aqueous dispersion, about 2 liters (0.002 cubic meters) of distilled water was supplied into the cyclone 10 by the pump described above for rinsing. After supplying distilled water, the concentrated dispersion was lyophilized by a well-known lyophilizes Subsequent to lyophilization, the procedure from aqueous dispersion production to lyophilization was repeated twice, in other words, the procedure from aqueous dispersion production to lyophilization was repeated three times in total.

[Results of Experiment Related to Example 9]

Results of the experiment related to Example 9 are shown in Table 3. Table 3 shows the treatment rate, the concentration ratio, the tubular member liquid average particle diameter, and the recovery rate in each round of the procedure described above. The concentration ratio is: volume of concentrated dispersion recovered/volume of aqueous dispersion supplied into cyclone×100.

TABLE 2

|  | Sampling time (seconds) | | | | | | | | |
| --- | --- | --- | --- | --- | --- | --- | --- | --- | --- |
|  | 60 | 120 | 240 | 360 | 480 | 600 | 720 | 840 | 960 |
| Midway-discharged liquid average particle diameter (μm) | 8.29 | 7.96 | 8.27 | 6.86 | 6.54 | 5.84 | 5.91 | 5.70 | 5.24 |
| Dry mass (kg/m³) | 6.08 | 5.40 | 4.36 | 4.43 | 3.96 | 3.31 | 3.69 | 3.71 | 3.61 |

TABLE 3

|  | Treatment rate | | Concentration ratio % | Tubular member liquid average particle diameter μm | Recovery rate % |
|---|---|---|---|---|---|
|  | L/min | m³/sec |  |  |  |
| 1st round | 2.00 | 3.33 × 10⁻⁵ | 33.8 | 5.4 | 86.7 |
| 2nd round | 2.00 | 3.33 × 10⁻⁵ | 32.4 | 5.6 | 86.0 |
| 3rd round | 2.00 | 3.33 × 10⁻⁵ | 36.7 | 5.3 | 80.4 |

Results in Table 3 clearly show that the treatment rate, the concentration ratio, the recovery rate, and the average particle diameter were reproducible.

Example 10

In this example, five cyclones each of which was the same as one in Example 7 were used. These cyclones were connected to a single well-known pump.

The procedure of this example is explained below. Into 40 liters (0.04 cubic meters) of a 0.01%-by-weight PVA solution, 240 g of a microcapsule powder was dispersed to give a product equivalent to an aqueous dispersion of a microcapsule. This product was an "aqueous dispersion" in this example. The microcapsule concentration in the aqueous dispersion was about 5.2 g/liter (about 5.2 kg/cubic meters). Subsequent to the production of the aqueous dispersion, the same procedure as in the concentration step S92 was carried out, where a microcapsule dispersion was recovered through a conical member outlet 50, a midway outlet 64, and a tubular member outlet 66. For 2 minutes (120 seconds) from the initiation of supplying the aqueous dispersion into the cyclone 10, a midway-discharged liquid was automatically mixed with the aqueous dispersion (this mixing was achieved by the connection established between the channel from the pump described above to the cyclone 10 and the channel in which the midway-discharged liquid traveled). A tubular member discharge liquid was discarded. When 120 seconds had passed since the initiation of supplying the aqueous dispersion into the cyclone 10, about 30 g (about 0.030 kg) of mannitol was added to the concentrated dispersion by an operator. After addition of mannitol, the concentrated dispersion was lyophilized by a well-known lyophilizer.

[Results of Experiment Related to Example 10]

In this example, the treatment rate was 16 liters/minute (0.000267 cubic meters/second). The concentration rate was 16.7 times. The recovery rate was 78.3%. The tubular member liquid average particle diameter was 5.7 micrometers. The average particle diameter in the midway-discharged liquid (at the time of 120 seconds in concentration) was 6.2 micrometers. The average particle diameter of the concentrated dispersion was 19.9 micrometers. The concentration rate was: volume of aqueous dispersion supplied into cyclone 10/volume of concentrated dispersion recovered.

Example 11

In this example, the same cyclone as in Example 7 described above was used. To the cyclone used in this example, a well-known pump was connected.

Figure 6:
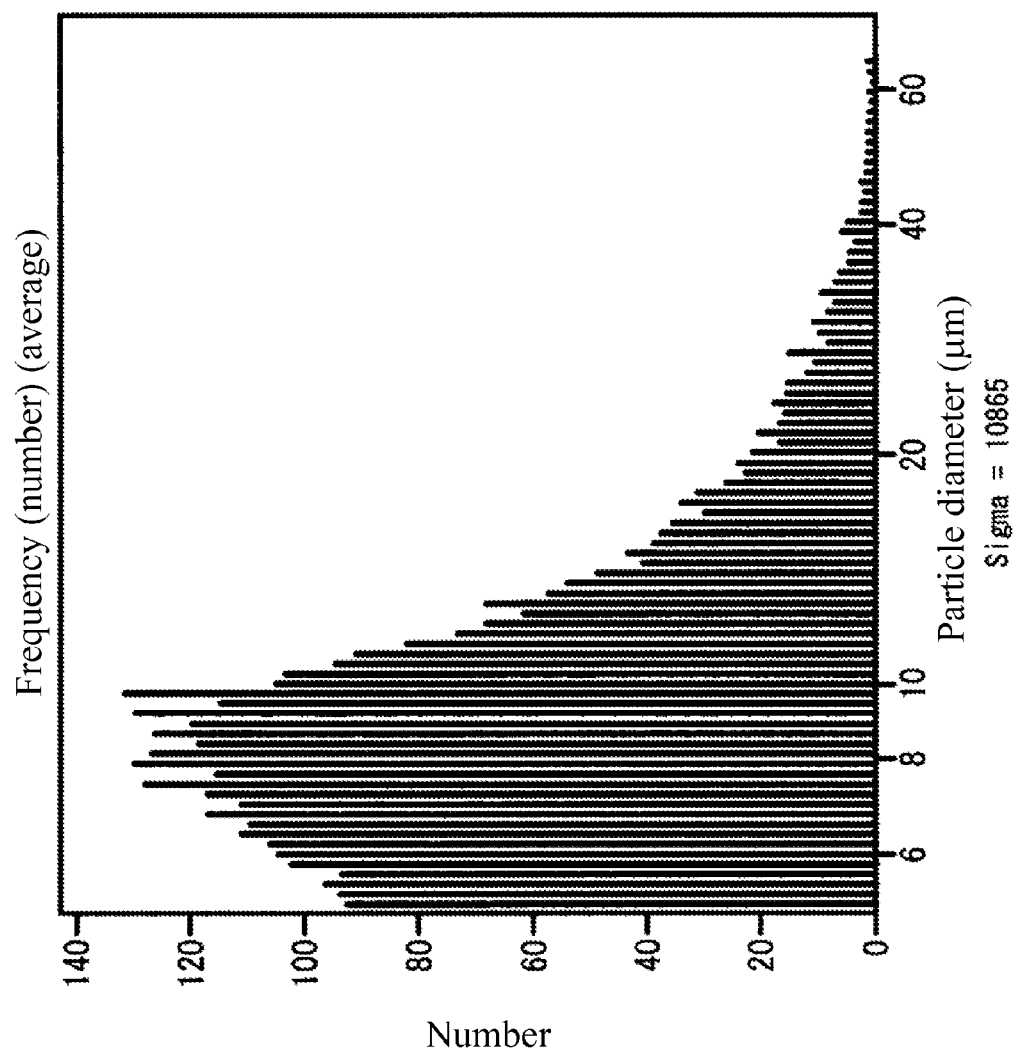
FIG. 6 shows the particle size distribution of a microcapsule of Example 11.

The procedure of microcapsule powder production in this example is explained below. In 252.5 g of dichloromethane, 138.0 g of a lactic acid-glycolic acid copolymer (ratio L/G=75/25, weight average molecular weight: 7800, manufactured by Wako Pure Chemical Industries, Ltd.) was dissolved, and 312.4 g of the resulting solution was mixed with a solution in which 14.8 g of a compound A powder was dissolved in 12.0 g of injectable distilled water. The resulting mixture was emulsified by a compact mixer (ROBOMIX manufactured by PRIMIX Corporation) (rotational speed: 10000 rpm, time: 60 seconds). As a result, a W/O emulsion was formed. The temperature of the W/O emulsion was then adjusted to 32° C. (305.15 K). After the temperature was adjusted, the W/O emulsion was injected into 20 liters (0.02 cubic meters) of a 0.01%-(w/w) aqueous polyvinyl alcohol (EG-40, manufactured by The Nippon Synthetic Chemical Industry Co., Ltd.) solution that had been adjusted to about 18° C. (291.15 K) in advance. The aqueous solution into which the W/O emulsion had thus been injected was subjected to secondary emulsification by a turbine homomixer (manufactured by Tokushu Kika Kogyo Co., Ltd.) (turbine rotational speed: about 7,000 rpm). As a result, a W/O/W emulsion was formed. The W/O/W emulsion was stirred for about 3 hours (in-water drying step), followed by sieving through a standard sieve of 75 micrometers. By this, microcapsules that did not pass through the standard sieve of 75 micrometers were removed from the W/O/W emulsion. After sieving, the W/O/W emulsion (in other words, an aqueous dispersion of a microcapsule) was concentrated by the cyclone 10 described above. A midway-discharged liquid was automatically mixed with the W/O/W emulsion in the same manner as in Example 1. When 12 minutes (720 seconds) had passed in concentration, part of the midway-discharged liquid not yet mixed with the W/O/W emulsion at that time was discarded. After 10 minutes (600 seconds) of concentration, 0.63 liters (6.3×10⁻⁴ cubic meters) of a concentrated dispersion was obtained. To the resulting concentrated dispersion, 16.0 g of mannitol was added. After addition of mannitol, the concentrated dispersion was lyophilized by a lyophilizes (DFM-05A-S custom-engineered by ULVAC, Inc.). As a result, a microcapsule powder was obtained. The treatment rate in this example was 1.9 liters/minute (3.17×10⁻⁵ cubic meters/second). The concentration rate in this example was 38.1 times. The recovery rate in this example was 74.4%. The average particle diameter of a microcapsule in a tubular member discharge liquid was 4.5 micrometers. The average particle diameter of a microcapsule in the midway-discharged liquid (at the time of 720 seconds in concentration) was 5.4 micrometers. The average particle diameter of a microcapsule powder resulting from lyophilization (concentrated dispersion average particle diameter) was 26.7 micrometers. The compound content in the microcapsule powder resulting from lyophilization was 8.4%. The particle size distribution of the microcapsule powder is shown in FIG. 6. In the graph in FIG. 6, the abscissa indicates the diameter of a microcapsule. In the graph, the ordinate indicates the number of microcapsules for a microcapsule powder. The number of microcapsules for a microcapsule powder was counted a plurality of times to prepare the graph. Each of the numbers shown in the graph indicates the average of the numbers thus counted.

Example 12

In this example, the same cyclone as in Example 7 described above was used. To the cyclone used in this example, a well-known pump was connected.

Figure 7:
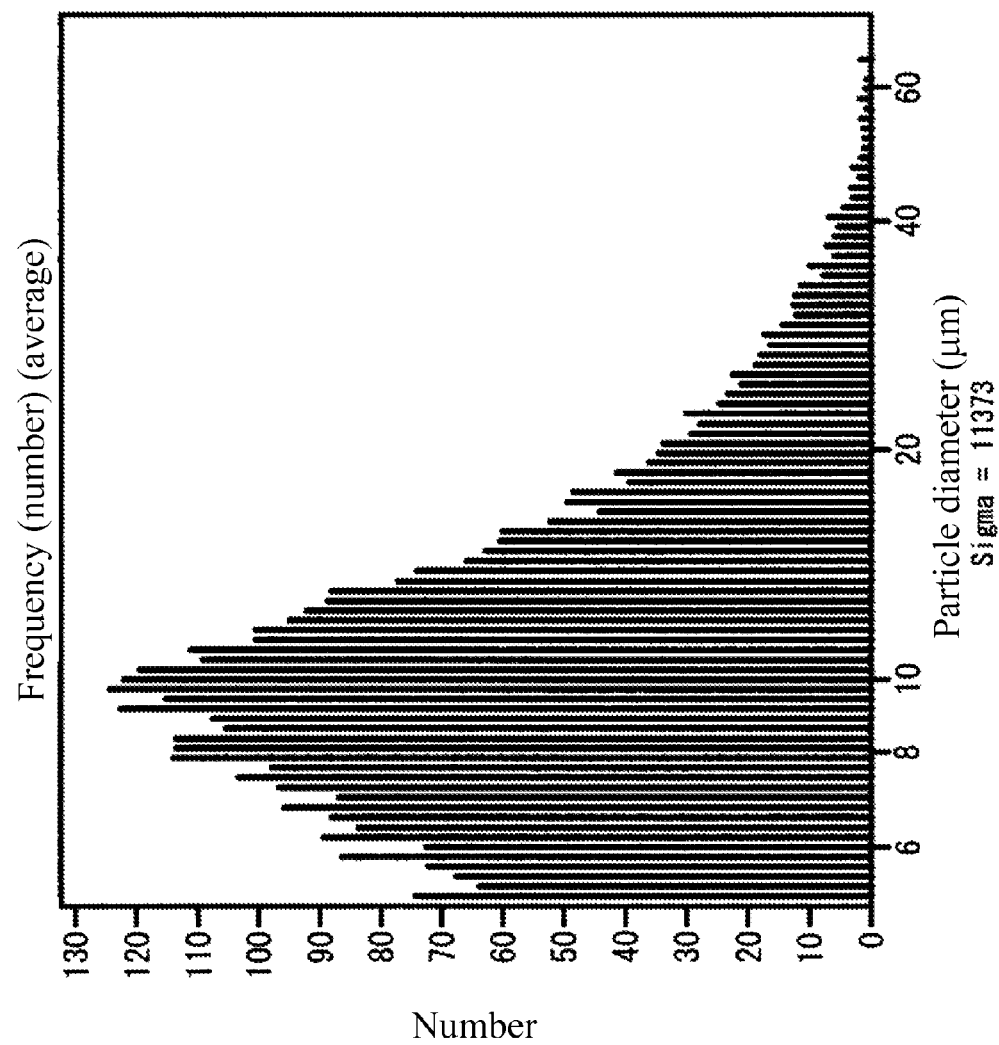
FIG. 7 shows the particle size distribution of a microcapsule of Example 12.

The procedure of microcapsule powder production in this example is explained below. In 12.0 g of deionized water, 12.0 g of a compound A powder was dissolved. In 252.5 g of dichloromethane, 138.0 g of a poly(lactic acid-glycolic acid) copolymer (ratio L/G=75/25, weight average molecular weight: 8200, manufactured by Wako Pure Chemical Industries, Ltd.) was dissolved, and 312.4 g of the resulting solution was mixed with the compound A aqueous solution described above. The resulting mixture was emulsified by a compact mixer (ROBOMIX manufactured by PRIMIX Corporation) (rotational speed: 10000 rpm, time: 60 seconds). As a result, a W/O emulsion was formed. The W/O emulsion was then injected into 40 liters (0.04 cubic meters) of a 0.01%-(w/w) aqueous polyvinyl alcohol (EG-40, manufactured by The Nippon Synthetic Chemical Industry Co., Ltd.) solution that had been adjusted to about 18° C. (291.15 K) in advance. The aqueous solution into which the W/O emulsion had thus been injected was subjected to secondary emulsification by a turbine homomixer (manufactured by PRIMIX Corporation) (turbine rotational speed: about 7,000 rpm). As a result, a W/O/W emulsion was formed. The W/O/W emulsion was stirred for about 3 hours (in-water drying step), followed by sieving through a standard sieve of 75 micrometers. By this, microcapsules that did not pass through the standard sieve of 75 micrometers were removed from the W/O/W emulsion. After sieving, the W/O/W emulsion (in other words, an aqueous dispersion of a microcapsule) was concentrated by the cyclone 10 described above. A midway-discharged liquid was automatically mixed with the W/O/W emulsion in the same manner as in Example 1. When 12 minutes (720 seconds) had passed in concentration, part of the midway-discharged liquid not yet mixed with the W/O/W emulsion at that time was discarded by an operator. After 10 minutes (600 seconds) of concentration, 0.68 liters ($6.8 \times 10^{-4}$ cubic meters) of a concentrated dispersion was obtained. To the resulting concentrated dispersion, 15.2 g of mannitol was added. After addition of mannitol, the concentrated dispersion was lyophilized by a lyophilizer (DFM-05A-S custom-engineered by ULVAC, Inc.). As a result, a microcapsule powder was obtained. The recovery rate was 67.5%. The compound content in the resulting microcapsule powder was 8.2%. The average particle diameter of the resulting microcapsule powder was 26.7 micrometers. The particle size distribution of the microcapsule powder is shown in FIG. 7. In the graph in FIG. 7, the abscissa indicates the diameter of a microcapsule. In the graph, the ordinate indicates the number of microcapsules for a microcapsule powder. The number of microcapsules for a microcapsule powder was counted a plurality of times to prepare the graph. Each of the numbers shown in the graph indicates the average of the numbers thus counted.

Studies conducted on Examples 11 and 12 proved that, by the method for producing a microcapsule powder according to an embodiment of the present invention, it is possible to produce a microcapsule powder that contains particles with a particle diameter of about 5 to about 70 μm and contains a low proportion of particles with a particle diameter of about 5 to about 10 μm.

Example 13

In this example, five cyclones each of which was the same as one in Example 7 described above were used. These cyclones were connected to a single well-known pump.

The procedure of microcapsule powder production in this example is explained below. In 525.2 g of dichloromethane, 315.0 g of a lactic acid-glycolic acid copolymer (ratio L/G=75/25, weight average molecular weight: 8200, manufactured by Wako Pure Chemical Industries, Ltd.) was dissolved, and 646.3 g of the resulting solution was mixed with 24.0 g of injectable distilled water. The resulting mixture was emulsified by a compact mixer (ROBOMIX manufactured by PRIMIX Corporation) (rotational speed: 10000 rpm, time: 60 seconds). As a result, a W/O emulsion was formed. The W/O emulsion was then injected into 40 liters (0.04 cubic meters) of a 0.01%-(w/w) aqueous polyvinyl alcohol (EG-40, manufactured by The Nippon Synthetic Chemical Industry Co., Ltd.) solution that had been adjusted to about 18° C. (291.15 K) in advance. The aqueous solution into which the W/O emulsion had thus been injected was subjected to secondary emulsification by a turbine homomixer (manufactured by PRIMIX Corporation) (turbine rotational speed: about 7,000 rpm). As a result, a W/O/W emulsion was formed. The W/O/W emulsion was stirred for about 3 hours (in-water drying step), followed by sieving through a standard sieve of 75 micrometers. By this, microcapsules that did not pass through the standard sieve of 75 micrometers were removed from the W/O/W emulsion. After sieving, the W/O/W emulsion (in other words, an aqueous dispersion of a microcapsule) was concentrated by the five cyclones 10 described above. A midway-discharged liquid was automatically mixed with the W/O/W emulsion in the same manner as in Example 1. When 12 minutes (720 seconds) had passed in concentration, part of the midway-discharged liquid not yet mixed with the W/O/W emulsion at that time was discarded. The amount of the resulting concentrated dispersion was 2.26 liters (0.00226 cubic meters). To the resulting concentrated dispersion, 30.0 g of mannitol was added. After addition of mannitol, the concentrated dispersion was lyophilized by a lyophilizer (DFM-05A-S custom-engineered by ULVAC, Inc.). As a result, a microcapsule powder was obtained. The treatment rate was 15.5 liters/minute ($2.583 \times 10^{-4}$ cubic meters/second). The concentration rate was 17.7 times. The recovery rate was 62.8%. The average particle diameter of a microcapsule in a tubular member discharge liquid was 4.3 micrometers. The average particle diameter of a microcapsule in the midway-discharged liquid (at the time of 120 seconds in concentration) was 5.6 micrometers. The average particle diameter of the microcapsule powder resulting from lyophilization was 23.6 micrometers.

Example 14

In this example, five cyclones each of which was the same as one in Example 7 described above were used. To these cyclones, a well-known pump was connected.

The procedure of microcapsule powder production in this example is explained below. In 4545.0 g of dichloromethane, 2700.0 g of a lactic acid-glycolic acid copolymer (ratio L/G=75/25, weight average molecular weight: 10000, manufactured by Wako Pure Chemical Industries, Ltd.) was dissolved, and 6440.0 g of the resulting solution was mixed with 240.0 g of injectable distilled water. The resulting mixture was emulsified by a compact mixer (ROBOMIX manufactured by PRIMIX Corporation) (rotational speed: 10000 rpm, time: 60 seconds). As a result, a W/O emulsion was formed. The W/O emulsion was then injected into 200 liters (0.200 cubic meters) of a 0.01%-(w/w) aqueous polyvinyl alcohol (EG-40, manufactured by The Nippon Synthetic Chemical Industry Co., Ltd.) solution that had been adjusted to about 18° C. (291.15 K) in advance. The aqueous solution into which the W/O emulsion had thus been injected was subjected to secondary emulsification by a turbine homomixer (manufactured by PRIMIX Corporation) (turbine rotational speed: about 7,000 rpm). As a result, a W/O/W emulsion was formed. The W/O/W emulsion was stirred for about 3 hours (in-water drying step), followed by sieving through a standard sieve of 75 micrometers. By this, microcapsules that did not pass through the standard sieve of 75 micrometers were removed from the W/O/W emulsion. After sieving, the W/O/W emulsion (in other words, an aqueous dispersion of a microcapsule) was concentrated by the five cyclones 10 described above. A midway-discharged liquid was automatically mixed with the W/O/W emulsion in the same manner as in Example 1. When 10 minutes (600 seconds) had passed in concentration, part of the midway-discharged liquid not yet mixed with the W/O/W emulsion at that time was discarded. To the resulting concentrated dispersion, 338.3 g of mannitol was added. After addition of mannitol, the concentrated dispersion was lyophilized by a lyophilizes (DFM-05A-S custom-engineered by ULVAC, Inc.). As a result, 1900.2 g of a microcapsule powder was obtained.

Example 15

In this example, the cyclone 10 shown in FIG. 2 described above was used. The material of the cyclone was SUS316L. To the cyclone 10, a well-known pump was connected.

Figure 8:
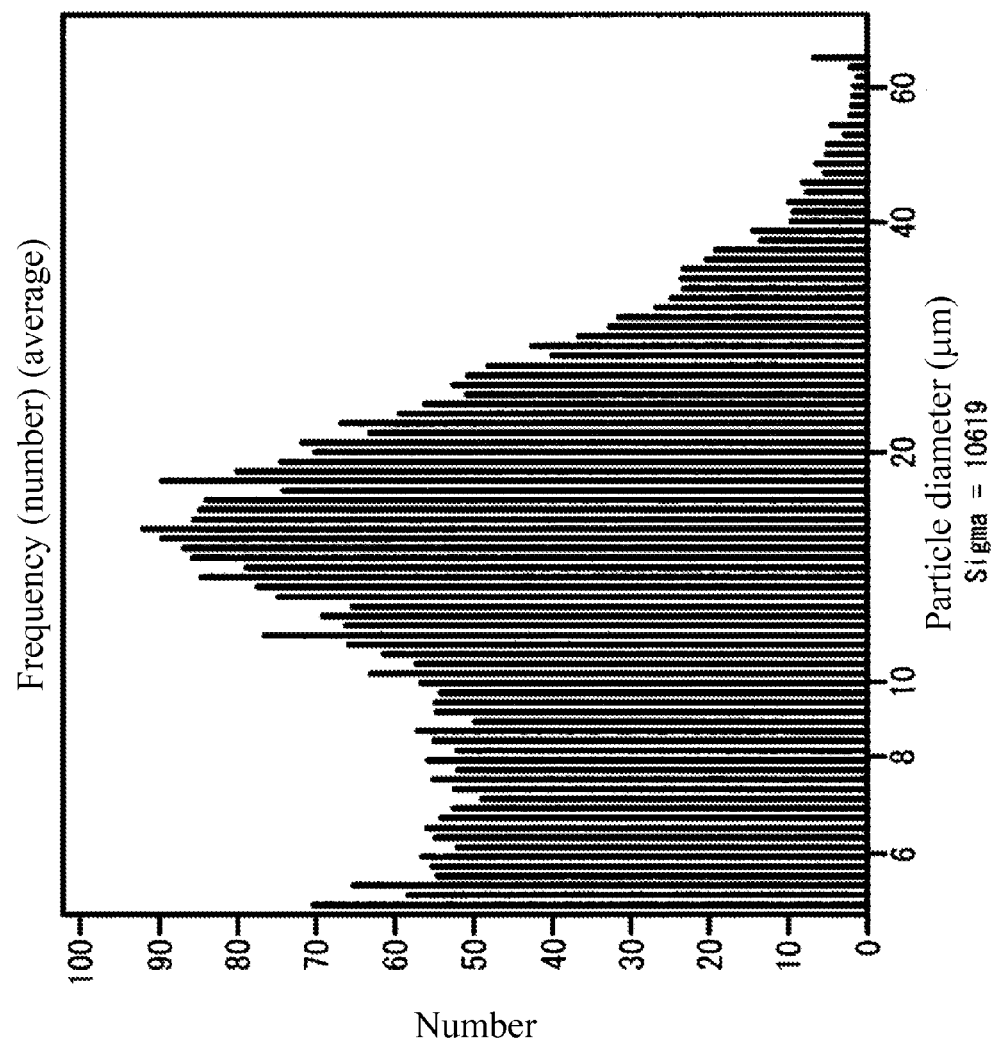
FIG. 8 shows the particle size distribution of a microcapsule of Example 17.

The procedure of microcapsule powder production in this example is explained below. In 12.0 g of deionized water, 14.8 g of a compound A powder (content: 81.2%) was dissolved. In 252.5 g of dichloromethane, 138.1 g of a lactic acid-glycolic acid copolymer (ratio L/G=75/25, weight average molecular weight: 8200, manufactured by Wako Pure Chemical Industries, Ltd.) was dissolved, and 312.5 g of the resulting solution was mixed with the compound A aqueous solution described above. The resulting mixture was emulsified by a compact mixer (ROBOMIX manufactured by PRIMIX Corporation) (rotational speed: 10000 rpm, time: 60 seconds). As a result, a W/O emulsion was formed. The W/O emulsion was then injected into 40 liters (0.04 cubic meters) of a 0.01%-(w/w) aqueous polyvinyl alcohol (EG-40, manufactured by The Nippon Synthetic Chemical Industry Co., Ltd.) solution that had been adjusted to about 18° C. (291.15 K) in advance. The aqueous polyvinyl alcohol solution was contained in a tank equipped with a homomixer (manufactured by PRIMIX Corporation). The aqueous solution into which the W/O emulsion had thus been injected was subjected to secondary emulsification by the homomixer (turbine rotational speed: about 7,000 rpm). As a result, a W/O/W emulsion was formed. The W/O/W emulsion was stirred for about 3 hours (in-water drying step), followed by sieving through a standard sieve of 75 micrometers. By this, microcapsules that did not pass through the standard sieve of 75 micrometers were removed from the W/O/W emulsion. After sieving, the W/O/W emulsion (in other words, an aqueous dispersion of a microcapsule) was concentrated by the cyclone 10 described above. A midway-discharged liquid and a tubular member discharge liquid were discarded. The amount of the resulting concentrated dispersion was 0.5 liters (0.0005 cubic meters). To the resulting concentrated dispersion, 15.2 g of mannitol was added. After addition of mannitol, the concentrated dispersion was lyophilized by a lyophilizer (DFM-05A-S custom-engineered by ULVAC, Inc.). As a result, a microcapsule powder was obtained. The recovery rate was 64.6%. The compound content in the resulting microcapsule powder was 7.3%. The average particle diameter of the resulting microcapsule powder was 31.0 micrometers. The particle size distribution of the microcapsule powder is shown in FIG. 8. In the graph in FIG. 8, the abscissa indicates the diameter of a microcapsule. In the graph, the ordinate indicates the number of microcapsules for a microcapsule powder. The number of microcapsules for a microcapsule powder was counted a plurality of times to prepare the graph. Each of the numbers shown in the graph indicates the average of the numbers thus counted.

FIG. 8 proves that, by the method for producing a microcapsule powder according to an embodiment of the present invention, it is possible to produce a microcapsule powder that contains particles with a particle diameter of about 5 to about 70 µm and contains a low proportion of particles with a particle diameter of about 5 to about 10 µm.

Figure 9:
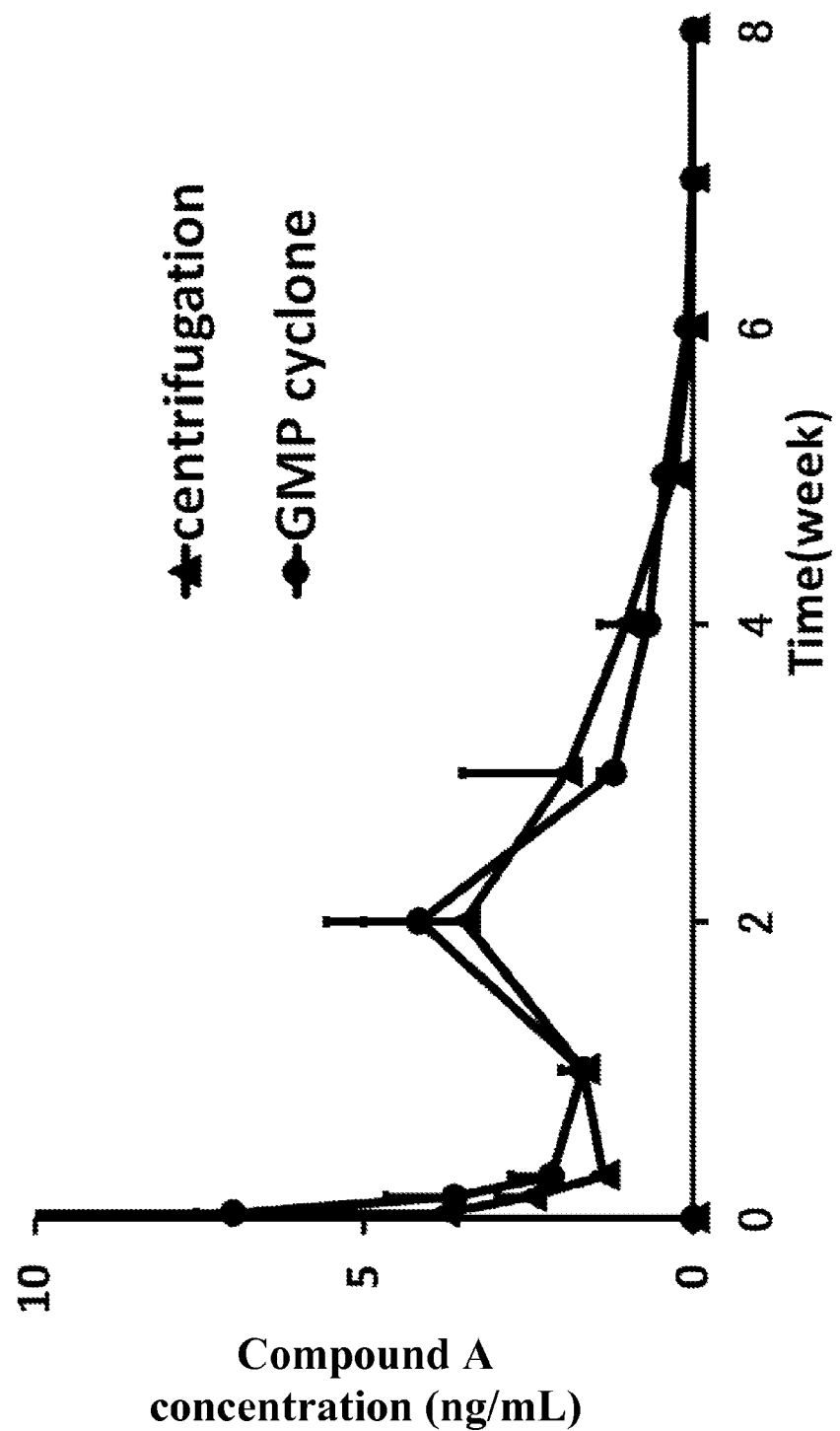
FIG. 9 shows the results of a test to evaluate a drug concentration in the blood of a rat when a microcapsule powder of Example 15 is used.

The microcapsule powder was subcutaneously injected into a rat (Jcl: SD, male, 7 weeks old at the time of administration) (1.6 mg/rat), and the rat was used in a test to evaluate a drug concentration in the blood. The results confirmed an excellent release of a drug from the microcapsule powder over 5 weeks or longer. Release of drug from the microcapsule powder was almost the same as that achieved by the microcapsule powder recovered by a centrifuge. The relationship between the drug concentration in the blood of the rat and time after subcutaneous injection is shown in FIG. 9. In the graph in FIG. 9, the ordinate indicates the concentration of the compound A in the blood. In the graph, the abscissa indicates the time after injection. The triangles in the graph indicate data for a microcapsule from which a liquid component has been removed by a centrifuge. The circles in the graph indicate data for the microcapsule in this example.

Example 16

In this example, the same cyclone 10 as in Example 15 described above was used. To the cyclone 10, a well-known pump was connected.

Figure 10:
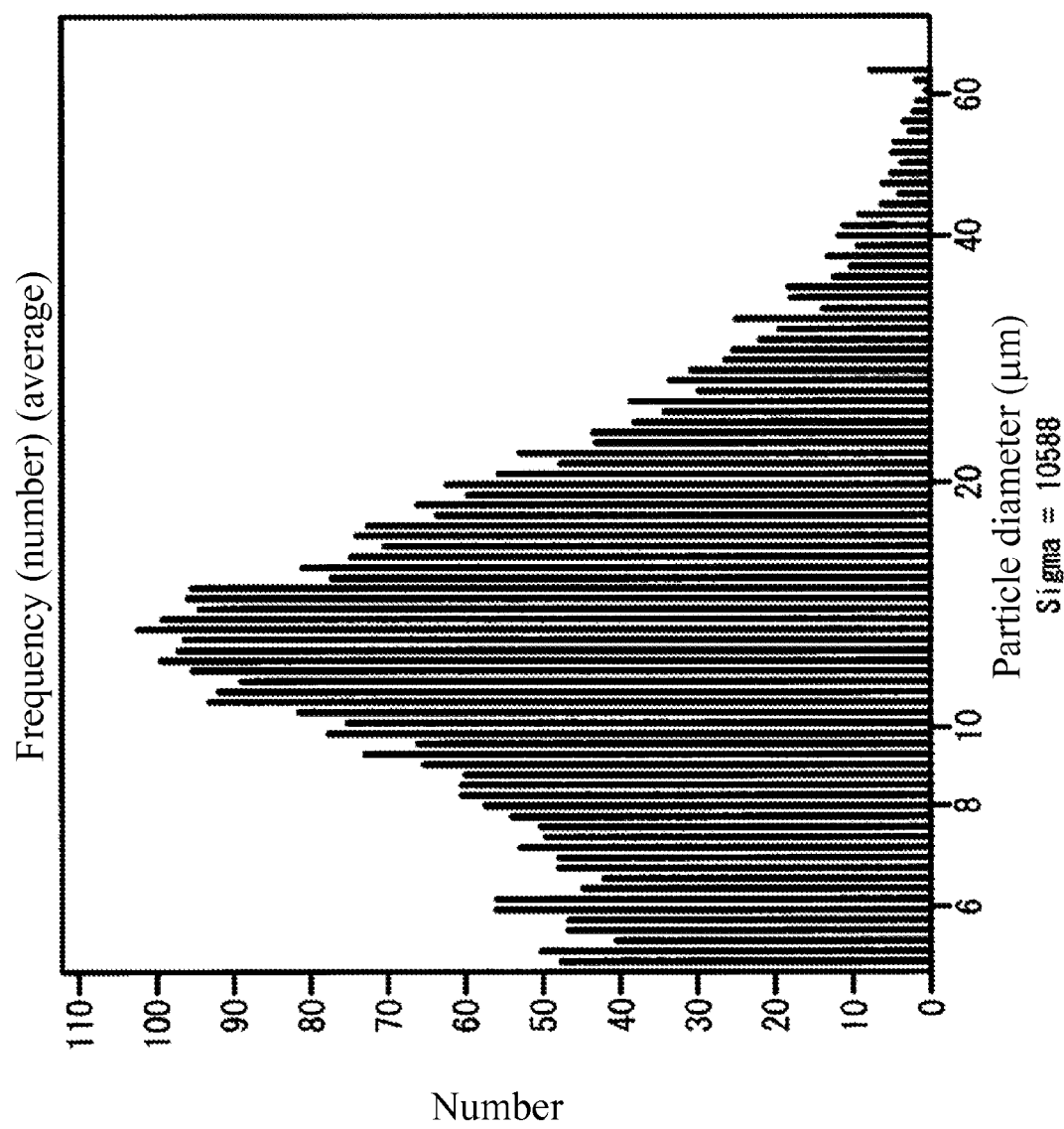
FIG. 10 shows the particle size distribution of a microcapsule of Example 10.

The procedure of microcapsule powder production in this example is explained below. In 84.0 g of methanol, 22.2 g of a compound A powder (compound content: 81.2%) was dissolved. In 223.1 g of dichloromethane, 130.4 g of a lactic acid-glycolic acid copolymer (ratio L/G=75/25, weight average molecular weight: 8000, manufactured by Wako Pure Chemical Industries, Ltd.) was dissolved, and 282.8 g of the resulting solution was mixed with the solution of the compound A in methanol described above. As a result, an O phase was formed. The O phase was then injected into 40 liters (0.04 cubic meters) of a 0.01%-(w/w) aqueous polyvinyl alcohol (EG-40, manufactured by The Nippon Synthetic Chemical Industry Co., Ltd.) solution that had been adjusted to about 18° C. (291.15 K) in advance. The aqueous polyvinyl alcohol solution was contained in a tank equipped with a homomixer (manufactured by PRIMIX Corporation). The aqueous solution into which the O phase had thus been injected was subjected to secondary emulsification by the homomixer (turbine rotational speed: about 7,000 rpm). As a result, an O/W emulsion was formed. The O/W emulsion was stirred for about 3 hours (in-water drying step), followed by sieving through a standard sieve of 75 micrometers. By this, microcapsules that did not pass through the standard sieve of 75 micrometers were removed from the O/W emulsion. After sieving, the O/W emulsion (in other words, an aqueous dispersion of a microcapsule) was concentrated by the cyclone 10 described above. A midway-discharged liquid and a tubular member discharge liquid were discarded. The amount of the resulting concentrated dispersion was 0.6 liters (0.0006 cubic meters). To the resulting concentrated dispersion, 16.9 g of mannitol was added. After addition of mannitol, the concentrated dispersion was lyophilized by a lyophilizes (DFM-05A-S custom-engineered by ULVAC, Inc.). As a result, 97.3 g of a microcapsule powder was obtained. The recovery rate was 74.8%. The compound content in the resulting microcapsule powder was 11.7%. The average particle diameter of the resulting microcapsule powder was 32.0 micrometers. The particle size distribution of the microcapsule powder is shown in FIG. 10. In the graph in FIG. 10, the abscissa indicates the diameter of a microcapsule. In the graph, the ordinate indicates the number of microcapsules for a microcapsule powder. The number of microcapsules for a microcapsule powder was counted a plurality of times to prepare the graph. Each of the numbers shown in the graph indicates the average of the numbers thus counted.

FIG. 10 proves that, by the method for producing a microcapsule powder according to an embodiment of the present invention, it is possible to produce a microcapsule powder that contains particles with a particle diameter of about 5 to about 70 µm and contains a low proportion of particles with a particle diameter of about 5 to about 10 µm.

Figure 11:
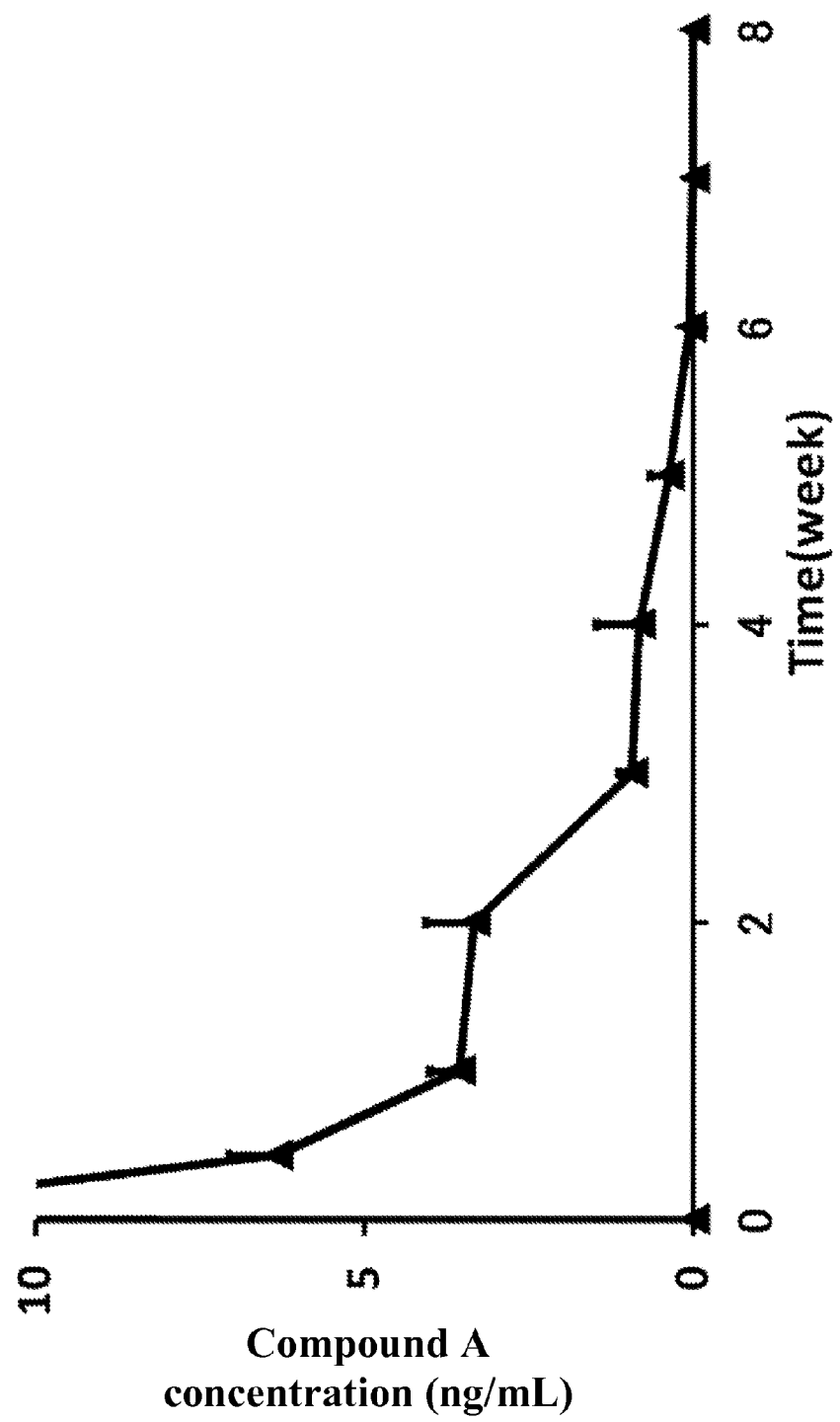
FIG. 11 shows the results of a test to evaluate a drug concentration in the blood of a rat when a microcapsule powder of Example 16 is used.

The microcapsule powder was subcutaneously injected into a rat (Jcl: SD, male, 7 weeks old at the time of administration) (1.6 mg/rat), and the rat was used in a test to evaluate a drug concentration in the blood. The results confirmed an excellent release of a drug from the microcapsule powder over 5 weeks or longer. The relationship between the drug concentration in the blood of the rat and time after subcutaneous injection is shown in FIG. 11. In the graph in FIG. 11, the ordinate indicates the concentration of the compound A in the blood. In the graph, the abscissa indicates the time after injection.

Figure 12:
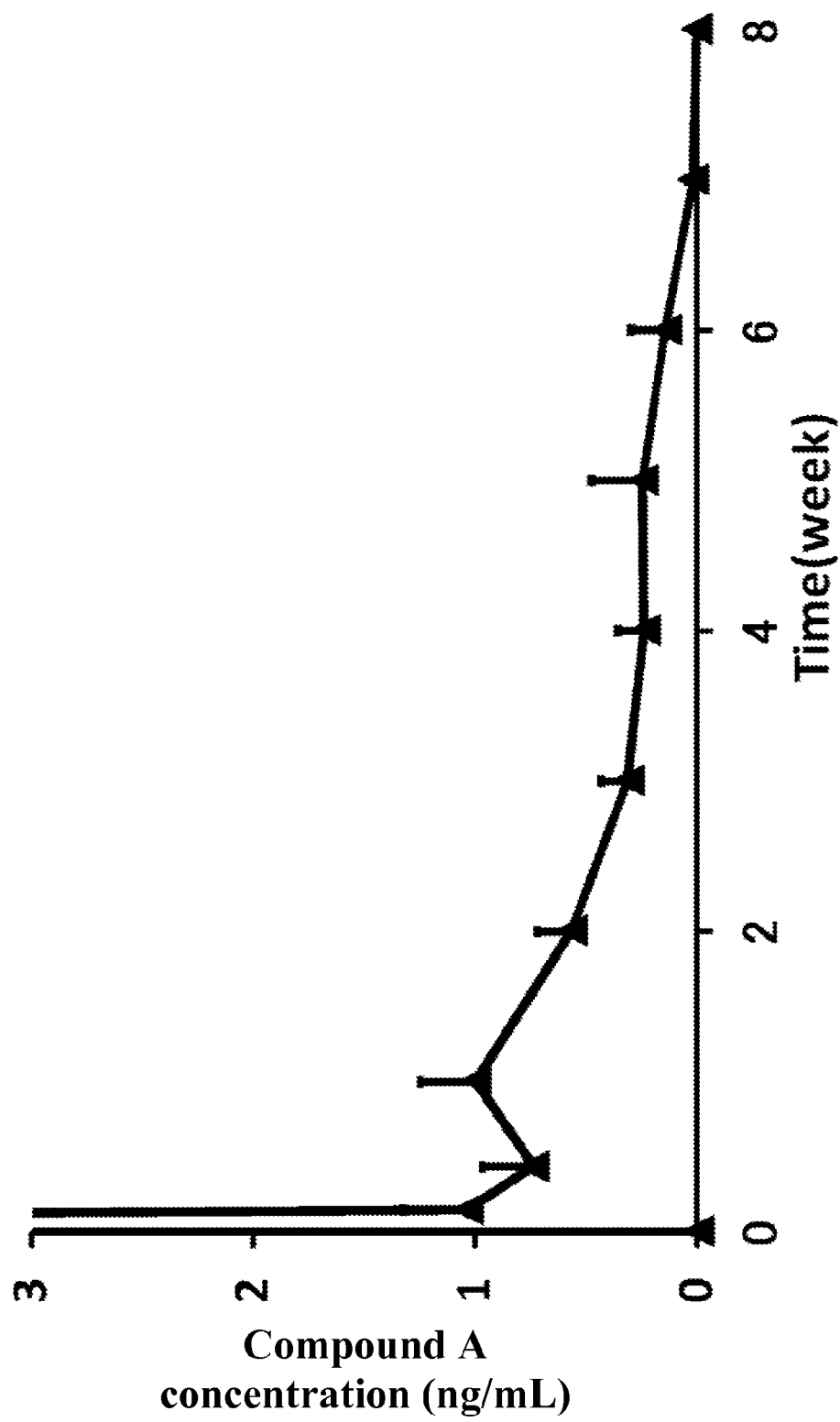
FIG. 12 shows the results of a test to evaluate a drug concentration in the blood of a dog when a microcapsule powder of Example 16 is used.

The microcapsule powder was subcutaneously injected into a dog (beagle, male, 8 to 9 months old at the time of administration) (0.5 mg/kg) as well, and the dog was used in a test to evaluate a drug concentration in the blood. The results confirmed an excellent release of a drug from the microcapsule powder over 6 weeks or longer. The relationship between the drug concentration in the blood of the dog and time after subcutaneous injection is shown in FIG. 12. In the graph in FIG. 12, the ordinate indicates the concentration of the compound A in the blood. In the graph, the abscissa indicates the time after injection.

Example 17

In this example, the same cyclone 10 as in Example 15 described above was used. To the cyclone 10, a well-known pump was connected.

Figure 13:
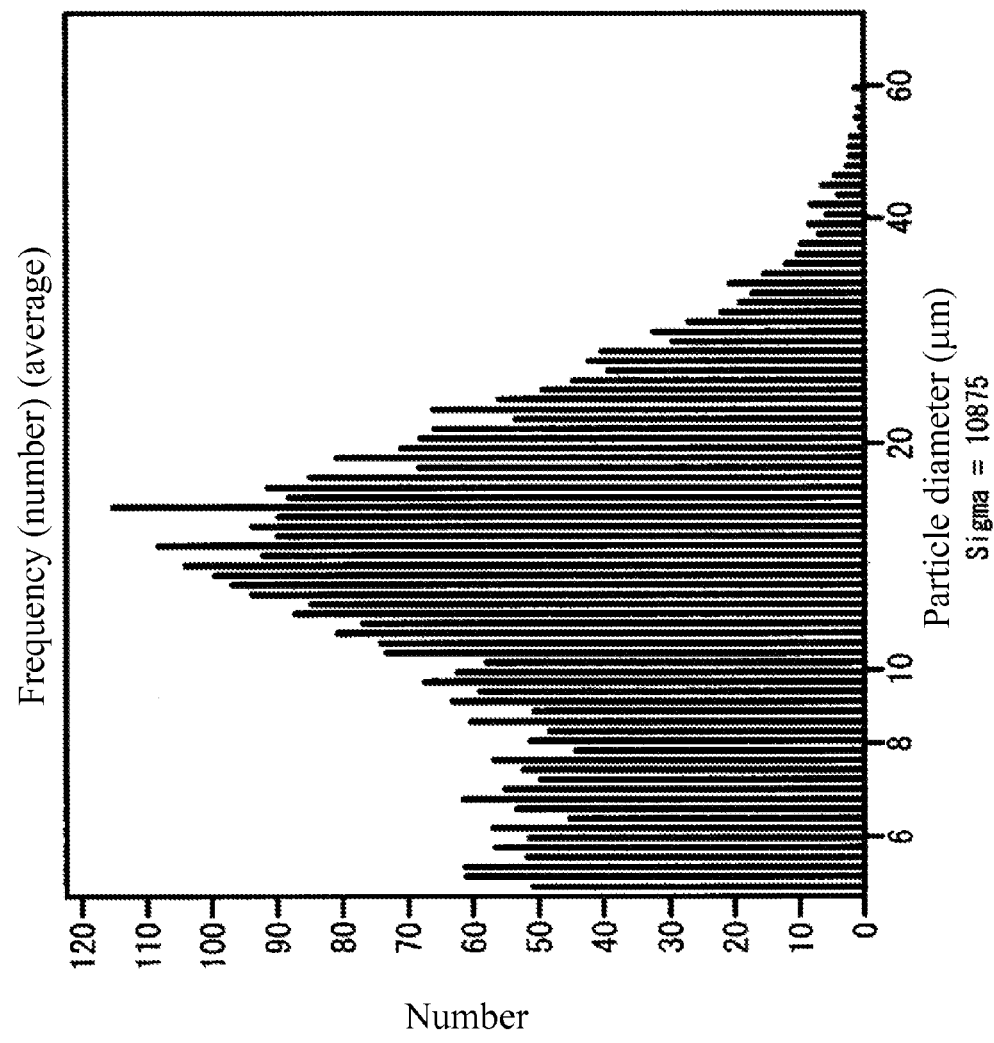
FIG. 13 shows the particle size distribution of a microcapsule of Example 17.

The procedure of microcapsule powder production in this example is explained below. In 84.0 g of methanol, 22.2 g of a compound A powder (content: 81.2%) was dissolved. As a result, a solution of the compound A in methanol was obtained. In 223.1 g of dichloromethane, 129.0 g of a lactic acid-glycolic acid copolymer (ratio L/G=75/25, weight average molecular weight: 7900, manufactured by Wako Pure Chemical Industries, Ltd.) was dissolved, and 281.7 g of the resulting solution was mixed with the solution of the compound A in methanol described above. As a result, an O phase was formed. The O phase was then injected into 40 liters (0.04 cubic meters) of a 0.01%-(w/w) aqueous polyvinyl alcohol (EG-40, manufactured by The Nippon Synthetic Chemical Industry Co., Ltd.) solution that had been adjusted to about 18° C. (291.15 K) in advance. The aqueous polyvinyl alcohol solution was contained in a tank equipped with a homomixer (manufactured by PRIMIX Corporation). The aqueous solution into which the O phase had thus been injected was subjected to secondary emulsification by the homomixer (turbine rotational speed: about 7,000 rpm). As a result, an O/W emulsion was formed. The O/W emulsion was stirred for about 3 hours (in-water drying step), followed by sieving through a standard sieve of 75 micrometers. By this, microcapsules that did not pass through the standard sieve of 75 micrometers were removed from the O/W emulsion. After sieving, the O/W emulsion (in other words, an aqueous dispersion of a microcapsule) was concentrated by the cyclone 10 described above. A midway-discharged liquid and a tubular member discharge liquid were discarded. The amount of the resulting concentrated dispersion was 0.53 liters (0.00053 cubic meters). To the resulting concentrated dispersion, 16.9 g of mannitol was added. After addition of mannitol, the concentrated dispersion was lyophilized by a lyophilizer (DFM-05A-S custom-engineered by ULVAC, Inc.). As a result, 95.9 g of a microcapsule powder was obtained. The recovery rate was 69.5%. The compound content in the resulting microcapsule powder was 11.9%. The average particle diameter of the resulting microcapsule powder was 26.6 micrometers. The particle size distribution of the microcapsule powder is shown in FIG. 13. In the graph in FIG. 13, the abscissa indicates the diameter of a microcapsule. In the graph, the ordinate indicates the number of microcapsules for a microcapsule powder. The number of microcapsules for a microcapsule powder was counted a plurality of times to prepare the graph. Each of the numbers shown in the graph indicates the average of the numbers thus counted.

FIG. 13 proves that, by the method for producing a microcapsule powder according to an embodiment of the present invention, it is possible to produce a microcapsule powder that contains particles with a particle diameter of about 5 to about 70 µm and contains a low proportion of particles with a particle diameter of about 5 to about 10 µm.

Figure 14:
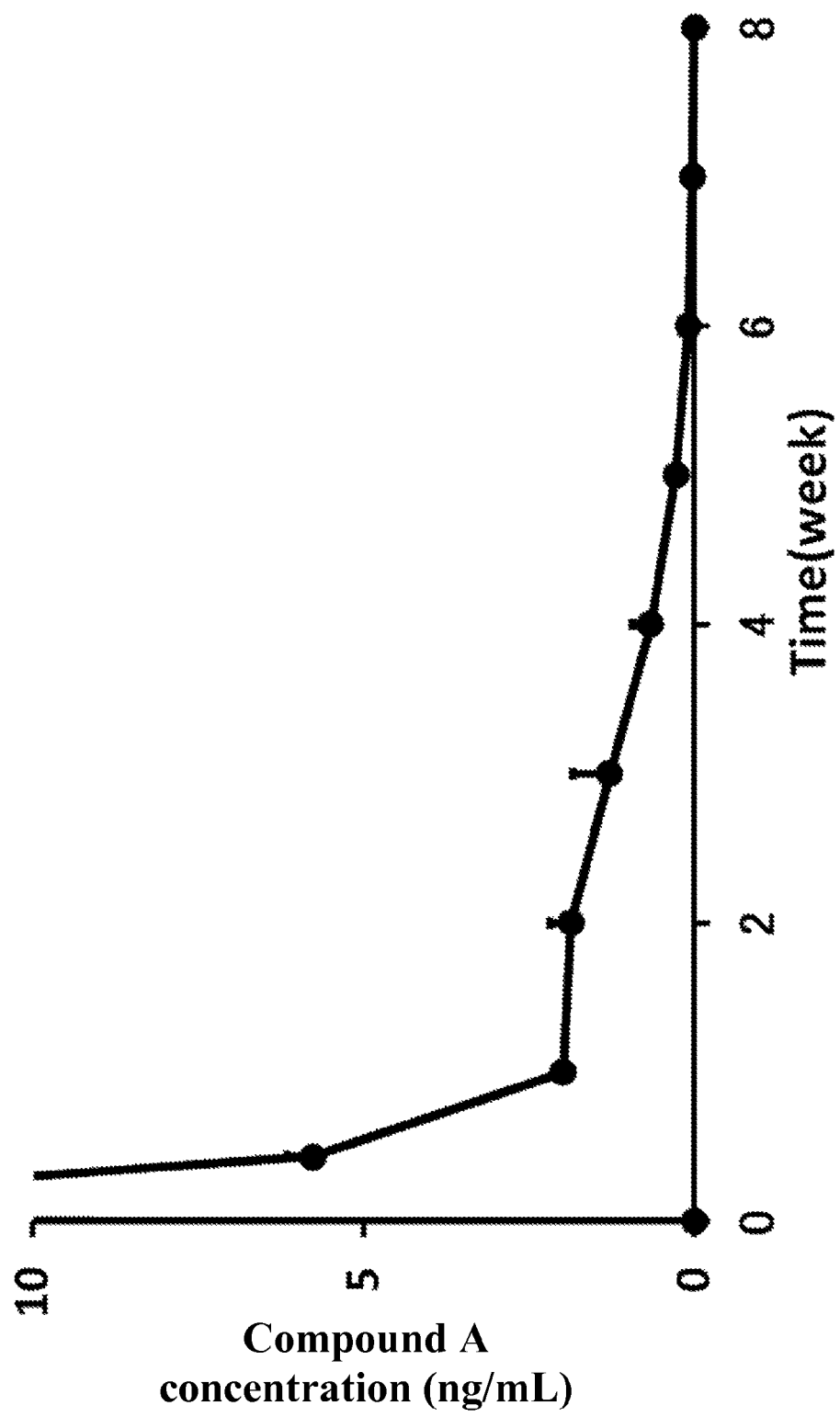
FIG. 14 shows the results of a test to evaluate a drug concentration in the blood of a rat when a microcapsule powder of Example 17 is used.

The microcapsule powder was subcutaneously injected into a rat (Jcl: SD, male, 7 weeks old at the time of administration) (1.6 mg/rat), and the rat was used in a test to evaluate a drug concentration in the blood. The results confirmed an excellent release of a drug from the microcapsule powder over 5 weeks or longer. The relationship between the drug concentration in the blood of the rat and time after subcutaneous injection is shown in FIG. 14. In the graph in FIG. 14, the ordinate indicates the concentration of the compound A in the blood. In the graph, the abscissa indicates the time after injection.

Figure 15:
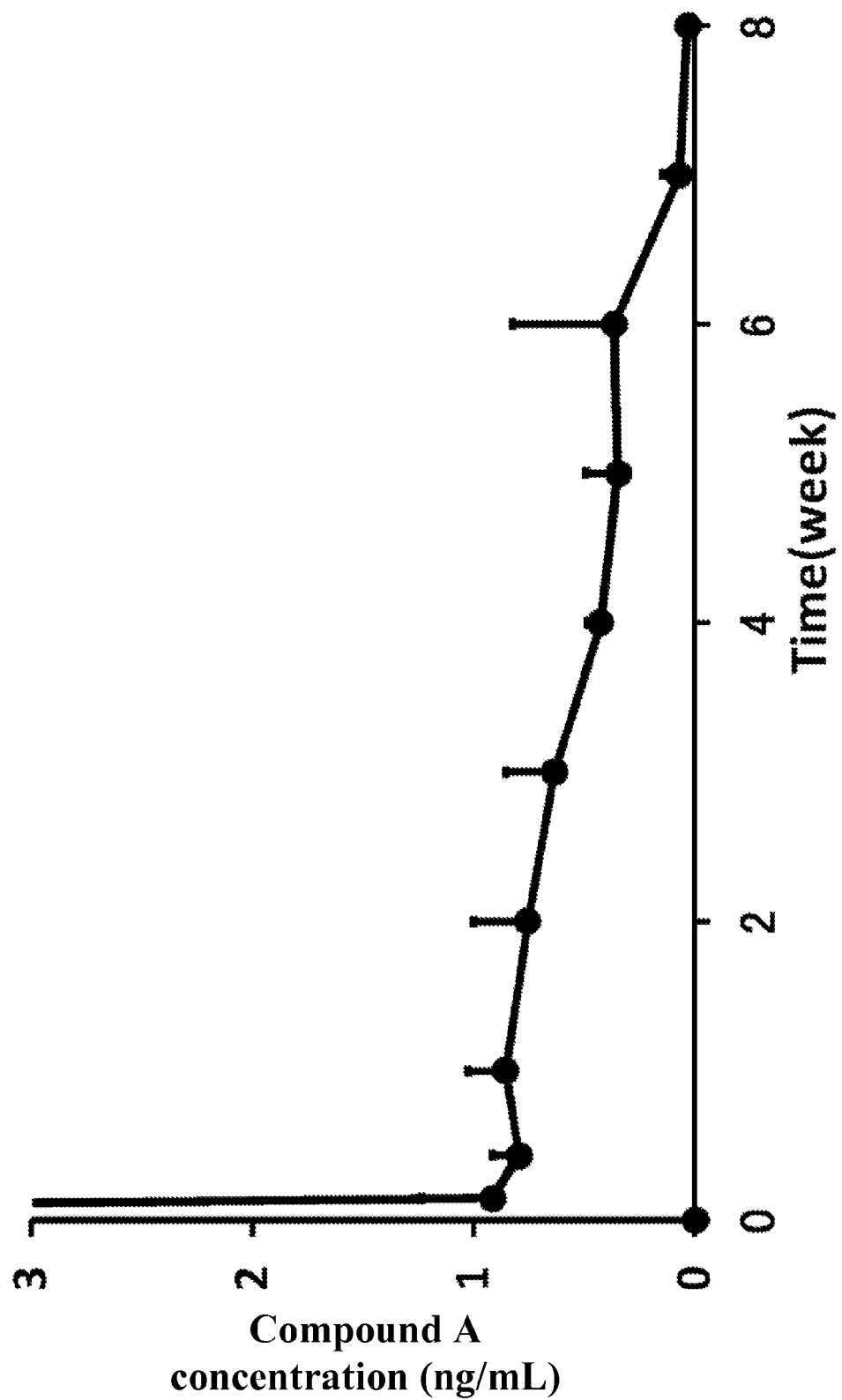
FIG. 15 shows the results of a test to evaluate a drug concentration in the blood of a dog when a microcapsule powder of Example 17 is used.

The microcapsule powder was subcutaneously injected into a dog (beagle, male, 8 to 9 months old at the time of administration) (0.5 mg/kg) as well, and the dog was used in a test to evaluate a drug concentration in the blood. The results confirmed an excellent release of a drug from the microcapsule powder over 6 weeks or longer. The relationship between the drug concentration in the blood of the dog and time after subcutaneous injection is shown in FIG. 15. In the graph in FIG. 15, the ordinate indicates the concentration of the compound A in the blood. In the graph, the abscissa indicates the time after injection.

Example 18

In this example, the same cyclone 10 as in Example 15 described above was used. To the cyclone 10, a well-known pump was connected.

Figure 16:
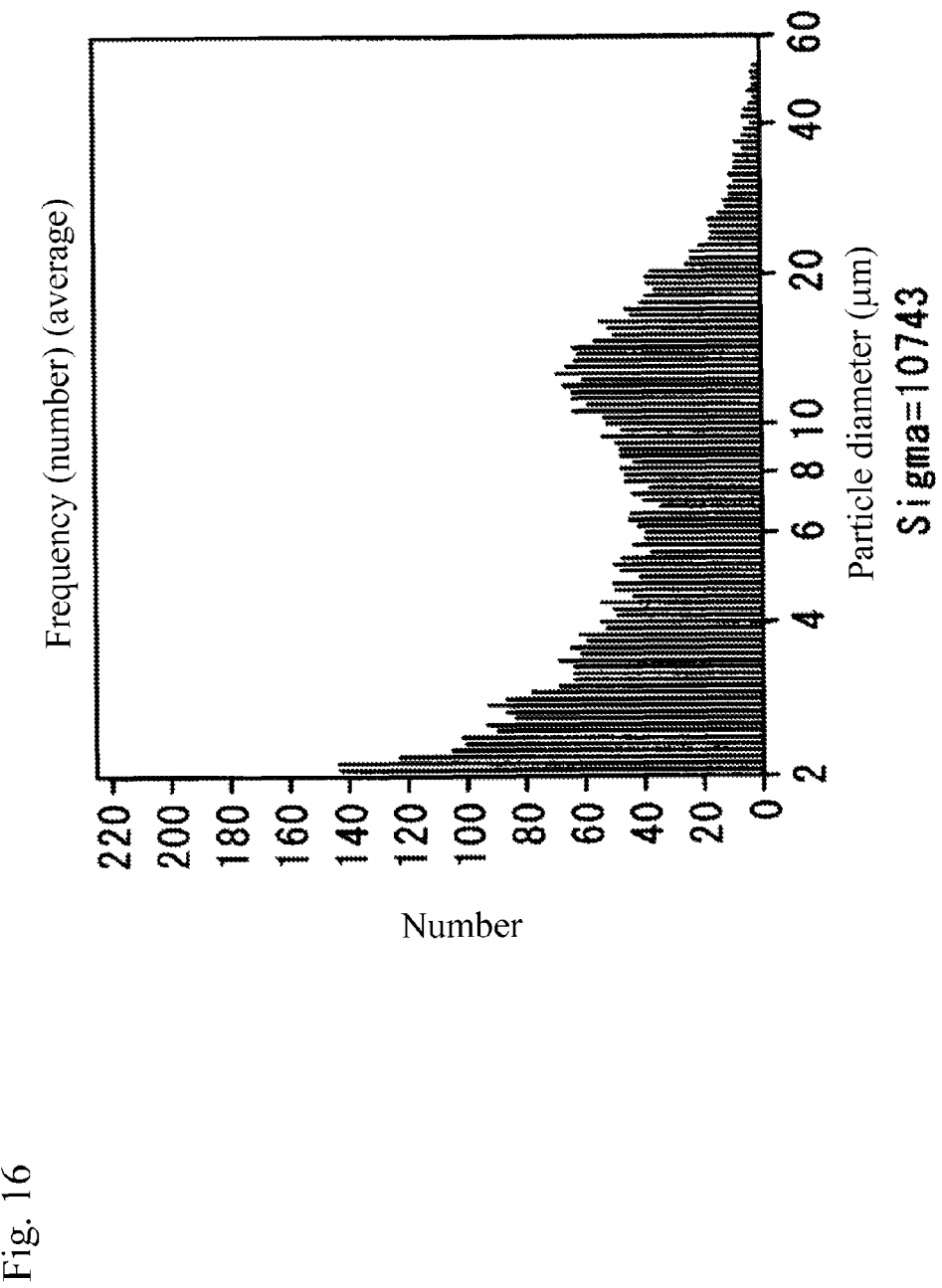
FIG. 16 shows the particle size distribution of a microcapsule of Example 18.

The procedure of microcapsule powder production in this example is explained below. In 12.0 g of purified water, 12.4 g of a compound B powder (content: 96.8%) was dissolved. As a result, a compound B aqueous solution was obtained. In 192.0 g of dichloromethane, 119.2 g of a lactic acid-glycolic acid copolymer (ratio L/G=75/25, weight average molecular weight: 11100, manufactured by Wako Pure Chemical Industries, Ltd.) was dissolved, and 259.3 g of the resulting solution was mixed with the compound B aqueous solution described above. The resulting mixture was emulsified by a compact mixer (ROBOMIX, manufactured by PRIMIX Corporation) (rotational speed: 10000 rpm, time: 30 seconds). As a result, a W/O emulsion was formed. The temperature of the W/O emulsion was then adjusted to about 18° C. (291.15 K). The W/O emulsion was then injected into 20 liters (0.02 cubic meters) of a 0.1%-(w/w) aqueous polyvinyl alcohol (EG-40, manufactured by The Nippon Synthetic Chemical Industry Co., Ltd.) solution that had been adjusted to about 18° C. (291.15 K) in advance. The aqueous polyvinyl alcohol solution was contained in a tank equipped with a homomixer (manufactured by PRIMIX Corporation). The aqueous solution into which the W/O emulsion had thus been injected was subjected to secondary emulsification by the homomixer (turbine rotational speed: about 7,000 rpm). As a result, a W/O/W emulsion was formed. The W/O/W emulsion was stirred for about 3 hours (in-water drying step), followed by sieving through a standard sieve of 75 micrometers. Part way through, 4 liters of purified water was added. By this, microspheres that did not pass through the standard sieve of 75 micrometers were removed from the W/O/W emulsion. Out of 20 liters (0.02 cubic meters) of the W/O/W emulsion (in other words, an aqueous dispersion of a microcapsule) resulting from sieving, 10 liters (0.01 cubic meters) was concentrated by the cyclone 10 described above. A midway-discharged liquid and a tubular member discharge liquid were discarded. The amount of the resulting concentrated dispersion was 0.20 liters (0.00020 cubic meters). To the resulting concentrated dispersion, 6.54 g of mannitol was added. After addition of mannitol, the concentrated dispersion was lyophilized by a lyophilizer (DFM-05A-S custom-engineered by ULVAC, Inc.). As a result, 22.7 g of a microcapsule powder was obtained. The recovery rate was 36.9%. The compound content in the resulting microcapsule powder was 3.2%. The average particle diameter of the resulting microcapsule powder was 28.1 micrometers. The particle size distribution of the microcapsule powder is shown in FIG. 16. In the graph in FIG. 16, the abscissa indicates the diameter of a microcapsule. In the graph, the ordinate indicates the number of microcapsules for a microcapsule powder. The number of microcapsules for a microcapsule powder was counted a plurality of times to prepare the graph. Each of the numbers shown in the graph indicates the average of the numbers thus counted.

FIG. 16 proves that, by the method for producing a microcapsule powder according to an embodiment of the present invention, it is possible to produce a microcapsule powder that contains a low proportion of particles with a particle diameter of about 5 to about 10 μm.

Precisely about 0.1 g of the microcapsule powder was weighed and placed in a 120-mL glass test vessel. Then, accurately 100 mL of a test liquid containing 0.02 mol/L of lactic acid, 0.1 (w/v) % of polysorbate 80, and 0.4 (w/v) % of polyvinyl alcohol was added. The glass test vessel was hermetically sealed with a rubber plug and then shaken 125 times (back-and-forth stroke) per minute at 48±0.5° C. The amount of the compound B released into the test liquid by 1 hour after initiation was measured to be 4.8%. In general, measurement of 15% or less in this test method is thought to indicate no problem in an initial release.

The microcapsule powder was subcutaneously injected into a rat (Jcl: SD, male, 7 weeks old at the time of administration) (0.9 mg/rat), and the rat was used in a test to evaluate a drug concentration in the blood. The results confirmed an excellent release of a drug from the microcapsule powder over 4 weeks or longer.

Example 19

In this example, a two-liquid classification cyclone was used. To the two-liquid classification cyclone, a well-known pump was connected.

The procedure of microcapsule powder production in this example is explained below. A compound B powder was dissolved in purified water to give a compound B aqueous solution. A lactic acid-glycolic acid copolymer was dissolved in dichloromethane. The resulting solution was mixed with the compound B aqueous solution described above, and the mixture thus obtained was emulsified by a compact mixer (ROBOMIX, manufactured by PRIMIX Corporation) (rotational speed: 10000 rpm, time: 30 seconds). As a result, a W/O emulsion was formed. The temperature of the W/O emulsion was then adjusted to about 18° C. (291.15 K). The W/O emulsion was then injected into a 0.1%-(w/w) aqueous polyvinyl alcohol (EG-40, manufactured by The Nippon Synthetic Chemical Industry Co., Ltd.) solution that had been adjusted to about 18° C. (291.15 K) in advance. The aqueous polyvinyl alcohol solution was contained in a tank equipped with a homomixer (manufactured by PRIMIX Corporation). The aqueous solution into which the W/O emulsion had thus been injected was subjected to secondary emulsification by the homomixer (turbine rotational speed: about 7,000 rpm). As a result, a W/O/W emulsion was formed. The W/O/W emulsion was stirred for about 3 hours (in-water drying step), followed by sieving through a standard sieve of 75 micrometers. Part way through, purified water was added. By this, microspheres that did not pass through the standard sieve of 75 micrometers were removed from the W/O/W emulsion. The W/O/W emulsion (in other words, an aqueous dispersion of a microcapsule) resulting from sieving was concentrated by the two-liquid classification cyclone described above. A midway-discharged liquid was discarded. To the resulting concentrated dispersion, mannitol was added. After addition of mannitol, the concentrated dispersion was lyophilized by a lyophilizer (DFM-05A-S custom-engineered by ULVAC, Inc.). As a result, a microcapsule powder was obtained.

[Explanation of Effects According to Embodiment of Present Invention]

In the method for producing a microcapsule powder according to an embodiment of the present invention, the cyclone 10 is used for concentrating an aqueous dispersion of a microcapsule to raise the microcapsule concentration. When the aqueous dispersion is thus concentrated, the time required for moisture removal can be easily reduced compared to the case where moisture is removed by a centrifuge or a filtration device. As a result, productivity in separating a microcapsule from the aqueous dispersion can be enhanced.

In the method for producing a microcapsule powder according to an embodiment of the present invention, the aqueous dispersion of a microcapsule is supplied into the cylindrical member inlet 40 of the cyclone 10, and a concentrated dispersion and a dilute dispersion are recovered from the cyclone 10. When the concentrated dispersion and the dilute dispersion are thus recovered from the cyclone 10, the time required for moisture removal can be easily reduced compared to the case where moisture is removed by a centrifuge or a filtration device because the ratio of removal from dispersion is easily reduced compared to the case where moisture is removed by a centrifuge or a filtration device. As a result, productivity in separating a microcapsule from the aqueous dispersion can be enhanced.

In the method for producing a microcapsule powder according to an embodiment of the present invention, the cyclone 10 has the relaxation member 26. The relaxation member 26 relaxes the strength with which a concentrated dispersion is discharged. Because of this, gushing of the concentrated dispersion out of the conical member outlet 50 can be inhibited. Because the gushing thus can be inhibited, scattering of the concentrated dispersion can be inhibited. Because the scattering thus can be inhibited, the yield of microcapsule production can be enhanced. Because the yield thus can be enhanced and the time required for moisture removal can be easily reduced, productivity in separating a microcapsule from an aqueous dispersion can be enhanced.

The method for producing a microcapsule powder according to an embodiment of the present invention comprises the lyophilization step S94. Moisture in the aqueous dispersion is partly removed in the concentration step S92 and, because of this, the fluidity of the aqueous dispersion at the start of the lyophilization step S94 can be high compared to the case where moisture is removed by a centrifuge or a filtration device. Because of the high fluidity thus achieved, a microcapsule can be easily transferred to start the lyophilization step S94. Because the microcapsule thus can be easily transferred, productivity can be enhanced correspondingly. The rest of the moisture in the aqueous dispersion is removed in the lyophilization step S94. This allows moisture to be removed at the completion of the lyophilization step S94 as in the case where a centrifuge or a filtration device is used to remove moisture from an aqueous dispersion. As a result, moisture can be removed as in the case where a centrifuge or a filtration device is used and productivity in separating a microcapsule from the aqueous dispersion can be enhanced.

The method for producing a microcapsule powder according to an embodiment of the present invention does not require manual recovery of a microcapsule by an operator. When manual recovery of a microcapsule by an operator is not necessary, the chances of an operator being exposed to a microcapsule or a chemical substance adhering thereto are lower than when manual recovery of a microcapsule is necessary. As the chances are thus reduced, the risk of harm to the health of an operator is reduced. In addition, less labor is required for ensuring safety so as to protect an operator from such a risk.

The method for producing a microcapsule powder according to an embodiment of the present invention, unlike in the case where a centrifuge or a filtration device is used for moisture removal, does not require manual scraping of a microcapsule off a centrifuge or a filtration device. When such scraping is necessary, additional measures are required for maintaining sterility at the time of scraping, while when such scraping is unnecessary, such additional measures are not required and, as a result, cost for implementing these measures becomes unnecessary.

DESCRIPTION OF REFERENCE SIGNS

10: Cyclone
20: Cylindrical member
22: Conical member
24: Tubular member
26: Relaxation member
30: Cylindrical space
32: Conical space
34: Flow-in space
40: Cylindrical member inlet
50: Conical member outlet
60: Outer tube
62: Inner tube
64: Midway outlet
66: Tubular member outlet
70, 72: Interior space
80: Flow-in port
82: Bend on flow-in side
84: Straight tubular portion
86: Bend on flow-out side
88: Concentrated dispersion flow-out port

The invention claimed is:

1. A method for producing a microcapsule powder, comprising a concentration step of supplying an aqueous dispersion of a microcapsule produced by in-water drying into a cyclone and then concentrating the aqueous dispersion to produce a concentrated dispersion, wherein the cyclone comprises:
   a cylindrical member having a cylindrical member inlet and defining a cylindrical space,
   a conical member attached to one end of the cylindrical member, defining a conical space, and having a conical member outlet,
   a tubular member attached to the other end of the cylindrical member and having a tubular member outlet,
   the conical space communicating with the cylindrical space, and
   the tubular member having an interior space that communicates with the cylindrical space; and
wherein the concentration step comprises:
   an aqueous dispersion-supplying step of supplying the aqueous dispersion into the cylindrical member inlet,
   a concentrated dispersion-recovering step of recovering the concentrated dispersion discharged through the conical member outlet, further comprising a dilute dispersion-recovering step of recovering a dilute dispersion having a microcapsule concentration lower than the microcapsule concentration in the concentrated dispersion.

2. The method according to claim 1, wherein:
the cyclone further comprises a midway outlet provided at a position that is closer to the tubular member outlet than the cylindrical member inlet is to the tubular member outlet and closer to the cylindrical member inlet than the tubular member outlet is to the cylindrical member inlet, and
the dilute dispersion-recovering step comprises a step of recovering a midway discharge liquid that is discharged through the midway outlet.

3. The method according to claim 1,
wherein the cyclone further comprises a relaxation member connected to the conical member, defining a flow-in space into which the concentrated dispersion discharged through the conical member outlet flows, and relaxing the strength with which the concentrated dispersion is discharged, and
wherein the concentrated dispersion-recovering step comprises:
   a flow-in step in which the concentrated dispersion flows out of the conical space into the flow-in space and, at the time of discharge through the conical member outlet, the concentrated dispersion receives pressure that is higher than the atmospheric pressure outside the relaxation member, and a discharge step of discharging the concentrated dispersion within the relaxation member out from the relaxation member.

4. The method according to claim 1, further comprising a step of lyophilizing the concentrated dispersion resulting from the concentration step.

5. The method according to claim 1, wherein the microcapsule contains a physiologically active substance.

6. The method according to claim 5, wherein the physiologically active substance is leuprorelin or a salt thereof.

* * * * *